(12) United States Patent
Roffler et al.

(10) Patent No.: US 8,491,891 B2
(45) Date of Patent: Jul. 23, 2013

(54) HUMAN BETA-GLUCURONIDASE MUTANTS WITH ELEVATED ENZYMATIC ACTIVITY UNDER PHYSIOLOGICAL CONDITIONS AND METHOD FOR IDENTIFYING SUCH

(75) Inventors: Steve Roffler, Taipei (TW); Chia-Hung Wu, Tainan (TW); Wolfgang Schechinger, Dieburg (DE); Kai-Chuan Chen, Kaohsiung (TW); Zeljko Prijovic, Belgrade (RS)

(73) Assignee: Academia Sinica, Taipei (TW)

( * ) Notice: Subject to any disclaimer, the term of this patent is extended or adjusted under 35 U.S.C. 154(b) by 575 days.

(21) Appl. No.: 12/625,795

(22) Filed: Nov. 25, 2009

(65) Prior Publication Data
US 2010/0129367 A1 May 27, 2010

Related U.S. Application Data

(60) Provisional application No. 61/193,411, filed on Nov. 26, 2008.

(51) Int. Cl.
*C07K 16/46* (2006.01)
*C12N 9/24* (2006.01)
*A61K 38/47* (2006.01)
*A61K 47/48* (2006.01)

(52) U.S. Cl.
CPC ........... *A61K 38/47* (2013.01); *A61K 47/48138* (2013.01); *C12N 9/2402* (2013.01); *Y10S 424/801* (2013.01); *Y10S 424/809* (2013.01)
USPC .................. 424/94.61; 424/178.1; 424/182.1; 424/801; 424/809; 530/391.1; 530/391.7; 435/183; 435/188; 435/188.5; 435/200; 514/1.3; 514/19.2; 514/19.3; 514/21.2; 514/21.3; 514/21.4; 514/21.5

(58) Field of Classification Search
USPC ............ 435/183, 188, 188.5, 200; 530/391.1, 530/391.7; 424/178.1, 182.1, 94.61, 801, 424/809; 514/1.3, 19.2, 19.3, 21.2, 21.3, 514/21.4, 21.5
See application file for complete search history.

(56) References Cited

U.S. PATENT DOCUMENTS 7,060,495 B2 * 6/2006 Gehrmann et al. ........ 424/94.61

OTHER PUBLICATIONS

Farokhzad, O.C., et al. Expert Opin. Drug Deliv. 3(30: 311-324, 2006.*
Muraro, R., et al. Cancer Res. 15: 48: 4588-4596, 1988.*
Kawato et al., "Intracellular Roles of SN-38, a Metabolite of the Camptothecin Derivative CPT-11, in the Antitumor Effect of CPT-11," Cancer Research, 51:4187-4191 (1991).
Kieke et al., "Selection of Functional T Cell Receptor Mutants from a Yeast Surface-Display Library," PNAS, 96:5651-5656 (1999).
Kim et al., "Shifting the pH Profile of *Aspergillus niger* PhyA Phytase to Match the Stomach pH Enhances its Effectiveness as an Animal Feed Additive," Applied and Environmental Microbiology 72(6):4397-4403 (2006).
Li et al., "Optimization of Humanized igGs in glycoengineered *Pichia pastoris*," Nature Biotechnology, 24(2):210-215 (2006).
Liao et al., "Design of Transgenes for Efficient Expression of Active Chimeric Proteins on Mammalian Cells," Biotechnology and Bioengineering, 73(4):313-323 (2001).
Lorincz et al., "Single Cell Analysis and Selection of Living Retrovirus Vector-corrected Mucopolysaccharidosis VII Cells Using a Fluorescence-Activated Cell Sorting-Based Assay for Mammalian β-Glucuronidase Enzymatic Activity," The Journal of Biological Chemistry, 274(2):657-665 (1999).
Makde et al., "Protein Engineering of Class-A Non-Specific Acid Phosphatase (PhoN) of *Salmonella typhimurium*: Modulation of the pH-Activity Profile," Biomolecular Engineering, 23:247-251 (2006).
Marais et al., "A Cell Surface Tethered Enzyme Improves Efficiency in Gene-Directed Enzyme ProDrug Therapy," Nature Biotechnology, 15 1373-1377 (1997).
Matsumura et al., "In vitro Evolution of a Novel Beta-galactosidase into a Beta-galactosidase Proceeds through Non-Specific Intermdiates," J. Mo. Biol. 305:331-339 (2001).
Mayer et al., "Modifying an Immunogenic Epitope on a Therapeutic Protein: A Step Towards an Improved System for Antibody-Directed Enzyme Prodrug Therapy (ADEPT)," British Journal of Cancer, 90:2402-2410 (2004).
Moolten, Frederick L., "Tumor Chemosensitivity Conferred by Inserted Herpes Thymidine Kinase Genes: Paradigm for a Prospective Cancer Control Strategy," Cancer Research, 46:5276-5281 (1986).
Morten et al., "Activation of CPT-11 in Mice: Identification and Analysis of a Highly Effective Plasma Esterase," Cancer Research 60:4206-4210 (2000).
Mullen et al., "Transfer of the Bacterial Gene for Cytosine Deaminase to Mammalian Cells Confers Lethal Sensitivity to 5-fluorocytosine: A Negative Selection System," PNAS, 89:33-37 (1992).
Murdter et al., "Dose Optimization of a Doxorubicin ProDrug (HMR 1826) in Isolated Perfused Human Lungs: Low Tumor pH Promotes Prodrug Activation by β-Glucuronidase," The Journal of Pharmacology and Experimental Therapeutics, 301(1):223-228 (2002).
Poujol et al., "Sensitive HPLC-Fluorescence Method for Irinotecan and Four Major Metabolites in Human Plasma and Saliva: Application to Pharmacokinetic Studies," Clinical Chemistry, 49:1900-1908 (2003).
Prijovich et al., "Effect of pH and Human Serum Albumin on the Cytotoxicity of a Glucuronide Prodrug of 9-aminocamptothecin," Cancer Chemother Pharmacol 60:7-17 (2007).
Prijovich et al., "Anti-Tumor Activity and Toxicity of the New Prodrug 9-aminocamptothecin Glucuronide (9ACG) in Mice," British Journal of Cancer, 86:1634-1638 (2002).

(Continued)

*Primary Examiner* — Misook Yu
*Assistant Examiner* — Anne Holleran
(74) *Attorney, Agent, or Firm* — Occhiuti Rohlicek & Tsao LLP

(57) ABSTRACT

A number of human beta-glucuronidase variants having higher enzymatic activity at physiological pH as compared with wild-type beta-glucuronidase and uses thereof in pro-drug therapy. Also disclosed herein is a method for identifying enzyme variants having elevated enzymatic activity using a mammalian surface display system.

11 Claims, 16 Drawing Sheets

OTHER PUBLICATIONS

Prijovich et al., "Stability of the new Produg 9-aminocamptothecin glucuronide (9ACG) in the Presence of Human Serum Albumin," Biochemical Pharmacology, 66:1181-1187 (2003).

Prijovich et al., "Local enzymatic Hydrolysis of an Engogenously Generated Metabolite Can Enhance CPT-11 Anticancer Efficacy," Mol. Cancer Ther., 8(4):940-946 (2009).

Rivory, Laurent P., "Metabolism of CPT-11: Impact on Activity," Annals New York Academy of Sciences, 205-215 (2000).

Russell, Alan J. and Alan R. Fersht, "Rational Modification of enzyme Catalysis by Engineering Surface Charge," Nature, 328:496-500 (1987).

Senter et al., "Anti-Tumor Effects of Antibody-Alkaline Phosphatase Conjugates in Combination with Etoposide Phosphate," PNAS, 85:4842-4846 (1988).

Sharma et al., "Effect of Cyclosporine on Immunogeniciy of a Bacterial Enzyme Carboxypeptidase G2 in ADEPT," Transplantation Proceedings, 28(6) 3154 (1996).

Shipley et al., "The Role of Glycosylation and Phosphorylation in the Expression of Active Human β-Glucuronidase," The Journal of Biological Chemistry, 268(16):12193-12198 (1993).

Smith et al., "Toward Antibody-directed Enzyme Prodrug Therapy with the T268G Mutant of Human Carboxypeptidase A1 and Novel in vivo Stable Prodrugs of Methotrexate," The Journal of Biological Chemistry, 272(25):15804-15816 (1997).

Sparreboom et al., "Irinotecan (CPT-11) Metabolism and Disposition in Cancer Patients," Clinical Cancer Research 4:2747-2754 (1998).

Spencer et al., "A Strategy for Mapping and Neutralizing Conformational Immunogenic sites on Protein Therapeutics," Proteomics, 2:271-279 (2002).

Stemmer, William P.C., "Rapid Evolution of a Protein in vitro by DNA Shuffling," Letters to Nature, 370:389-391 (1994).

Sternberg et al., "Prediction of Electrostatic Effects of Engineering of Protein Charges," Nature, 330:86-89 (1987).

Su et al., "Gene Expression Imaging by Enzymatic Catalysis of a Fluorescent Probe via Membrane-Anchored β-Glucuronidase," Gene Therapy, pp. 1-10 (2001).

Telford et al., "Detection of Endogenous and Antibody-Conjugated Alkaline Phosphatase with ELF-97 Phosphate in Multicolor Flor Cytometry Applications," Cytometry. 43:117-125 (2001).

Wang, Xin Xiang, and Eric V. Shusta, "The Use of scFv-Displaying Yeast in Mammalian Cell Surface Selections," Journal of Immunological Methods, 304:30-42 (2005).

Wang et al., "Specific Activation of Glucuronide Prodrugs by Antibody-targeted Enzyme Conjugates for Cancer Therapy," Cancer Research 52:4484-4491 (1992).

Angenault et al., "Cancer Chemotherapy: A SN-38 (7-Ethyl-10-hydroxycamptothecin) Glucuronide Prodrug for Treatment by a PMT (Prodrug MonoTherapy) Strategy," Bioorganic & Medicinal Chemistry Letters, 13:947-950 (2003).

Bagshawe, K.D., and S.K. Sharma, "Cyclosporine Delays Host Immune Responses to Antibody Enzyme Conjugate in ADEPT," Transplantation Proceedings, 28(6):3156-3158 (1998).

Border, Eric T., and K. Dane Wittrup, "Yeast Surface Display for Screening Combinatorial Polypeptide Libraries," Nature Biotechnology, 15:553-557 (1997).

Border, Eric T., and K. Dane Wittrup, "Yeast Surface Display for Directed Evolution of Protein Expression, Affinity and Stability," Methods in Enzymology, 328:430-444 (2000).

Chen et al., "Potentiation of Antitumor Immunity by Antibody-Directed Enzyme Prodrug Therapy," Int. J. Cancer, 94:850-858 (2001).

Chen et al., "Membrance-localized Activation of Glucuronide Prodrugs by β-Glucuronidase Enzymes," Cancer Gener Therapy, 1-14 (2006).

Chen et al., "Directed Evolution of a Lysosomal Enzyme with Enhanced Activity at Neutral pH by Mammalian Cell-Surface Display," Chemistry & Biology, 15:1277-1286 (2008).

Cheng et al., "Bystander Killing of Tumor Cells by Antibody-Targeted Enzymatic Activation of a Glucuronide Prodrug," British Journal of Cancer, 79:1378-1385 (1999).

Cheng et al., "Characterization of Antineoplastic Glucuronide Prodrug," Biochemical Pharmacology, 58:325-328 (1999).

Cheng et al., "Hapten-Directed Targeting to Sing-Chain Antibody Receptors," Cancer Gene Therapy, 11:380-388 (2004).

Cheng et al.,"Tumor-Targeting Prodrug-Activating Bacteria for Cancer Therapy," Cancer Gene Therapy, 15:393-401 (2008).

Chou et al., "Expression of Chimeric Monomer and Dimer Proteins on the Plasma Membrance of Mammalian Cells," Biotechnol Bioeng, 65:160-169 (1999).

M de Graaf et al., "A Fully Human Anti-Ep-CAM scFv-beta-glucuronidase Fusion Protein for Selective Chemotherapy with a Glucuronide Prodrug," British Journal of Cancer, 86:811-818 (2002).

Dodds et al., "The Importance of Tumor Glucuronidase in the Activation of Irinotecan in a Mouse Xenograft Model, " The Journal of Pharmacology and Experimental Therapeutics, 309(2):649-655 (2002).

Geddie, Melissa L. and Ichiro Matsumura, "Rapid Evolution of β-Glucuronidase Specificity by Saturation Mutagenesis of an Active Site Loop," The Journal of Biological Chemistry, 270(15):26462-26468 (2004).

Heine et al., "Cell Surface Display of a Lysosomal Enzyme for Extracellular Gene-Directed Enzyme Prodrug Therapy," Gene Therapy, 8:1005-1010 (2001).

Houba et al., "Distribution and Pharmacokinetics of the Prodrug Daunorubicin-GA3 in Nude Mice Bearing Human Ovarian Cancer Xenografts," Biochemical Pharmacology, 57:673-680 (1999).

Islam et al., "Active Site Residues of Human β-Glucuronidase," The Journal of Biological Chemistry, 274(33):23451-23455 (1999).

Juan et al., "Antiangiogenesis Targeting Tumor Microenvironment Synergizes Glucuronide Prodrug Antitumor Activity," Clin Cancer Res 15(14):4600-4611 (2009).

Kaur, Jasjeet and Rohit Sharma, "Directed Evolution: An Approach to Engineer Enzymes," Critical Reviews in Biotechnology, 26:165-199 (2006).

* cited by examiner

HUMAN BETA-GLUCURONIDASE MUTANTS WITH ELEVATED ENZYMATIC ACTIVITY UNDER PHYSIOLOGICAL CONDITIONS AND METHOD FOR IDENTIFYING SUCH

RELATED APPLICATION

This application claims priority to U.S. Provisional Application No. 61/193,411, filed on Nov. 26, 2008, the content of which is hereby incorporated by reference in its entirety.

BACKGROUND OF THE INVENTION

Although chemotherapy is an important treatment modality for advanced cancers, many anti-cancer drugs have limited therapeutic efficacy due to high systemic toxicity and lack of tumor selectivity. Several non-toxic prodrugs (e.g., glucuronide prodrugs) have been developed. These prodrugs, when converted to active drugs at a tumor site, exert high chemotherapy efficacy.

Typically, a prodrug is metabolized in vivo, preferably at the tumor site, to an active drug via enzyme digestion. Human lysosomal hydrolases (e.g., beta-glucuronidase) are ideal enzymes for use in prodrug therapy as they do not induce immune responses in human patients. However, the use is hindered by the low activity of these enzymes at physiological pH.

It has been of great interest to identify hydrolase variants that preserve enzymatic activity under physiological conditions, such as neutral pH.

SUMMARY OF THE INVENTION

The present invention is based on unexpected identification of five human beta-glucuronidase variants that exhibit higher enzymatic activity at neutral pH as compared to their wild-type counterpart.

Accordingly, one aspect of this invention features polypeptides including amino acid sequences at least 95% identical to SEQ ID NOs:6-10 (shown below), the amino acid sequences of the five human beta-glucuronidase variants mentioned above. These polypeptides can each be fused with a cancer-targeting single-chain antibody (e.g., a human or humanized antibody) or a cancer-targeting peptide to form a fusion protein. It can otherwise be conjugated with a cancer-targeting agent (e.g., a single-chain antibody, a peptide, or an aptamer) to form a conjugate. As used herein, "conjugated" refers to association of two entities via covalent bonding, noncovalent bonding, or entrapment (e.g., one entity on or within the other, or either or both entities on or within a third entity that can be a micelle), the associating having sufficient affinity so that the therapeutic benefit of the association between the two entities is realized.

Another aspect of the invention is a nucleic acid including a nucleotide sequence encoding one of the human beta-glucuronidase variants, one of the fusion proteins described above, or a fusion protein containing one of the beta-glucuronidase variants and a cell membrane anchoring domain. In one example, the nucleic acid is a DNA construct designed for expressing the human beta-glucuronidase variant on cancer cell surfaces.

In yet another aspect, the invention features a prodrug cancer therapy using any of these human beta-glucuronidase variants or a nucleic acid encoding it. This therapeutic method includes delivering to cancer cells in a cancer patient a human beta-glucuronidase variant described above by, e.g., administering to the patient the beta-glucuronidase variant either fused or conjugated with a cancer targeting agent, or a DNA construct for expressing the beta-glucuronidase variant in the cancer cells. The method further includes administering to the patient an effective amount of an anti-cancer prodrug. The prodrug is either an anti-cancer glucuronide prodrug (e.g., SN-38G, 9ACG, HAMG, doxorubicin glucuronide, paclitaxel glucuronide, daunomycin glucuronide, 5-fluorouracil glucuronide, epirubicin glucuronide, etoposide glucuronide, duocarmycin glucuronide, and CC-1065 glucuronide) or a compound (e.g., CPT-11) that converts to a glucuronide prodrug in vivo.

Any of the human beta-glucuronidase variants mentioned above or a nucleic acid encoding it, together with an anti-cancer prodrug, can be used in treating cancer or in manufacturing of a medicament for cancer treatment.

Further, the present invention features a method of identifying a variant of an enzyme (e.g., a lysosomal acid hydrolase) having elevated enzymatic activity under a desired condition (e.g., a physiological condition), as compared to its wild-type counterpart. This method includes at least four steps: (i) providing a plurality of mammalian cells, which display on their surfaces variants of an enzyme (e.g., human beta-glucuronidase); (ii) examining enzymatic activity of surface-displayed variants of the enzyme under defined conditions (e.g., neutral pH); (iii) identifying a cell that displays a variant of the enzyme having enzymatic activity higher than that of its wild-type counterpart; and (iv) collecting the cell for characterization of the variant. To display the enzyme variants on cell surfaces, each variant can be fused with a cell membrane anchoring domain, which can be derived from antigen B7-1. Preferably, each cell displays one copy of an enzyme variant on its surface. When beta-glucuronidase variants are the targets, the examining step can be performed by contacting the cells with ELF97 beta-D-glucuronide and determining cell surface fluorescent levels by, e.g., fluorescence-activated cell sorting.

The details of one or more embodiments of the invention are set forth in the description below. Other features or advantages of the present invention will be apparent from the following drawings and detailed description of several examples, and also from the appended claims.

BRIEF DESCRIPTION OF THE DRAWINGS

The drawings are first described.

DETAILED DESCRIPTION OF THE INVENTION

Figure 1:
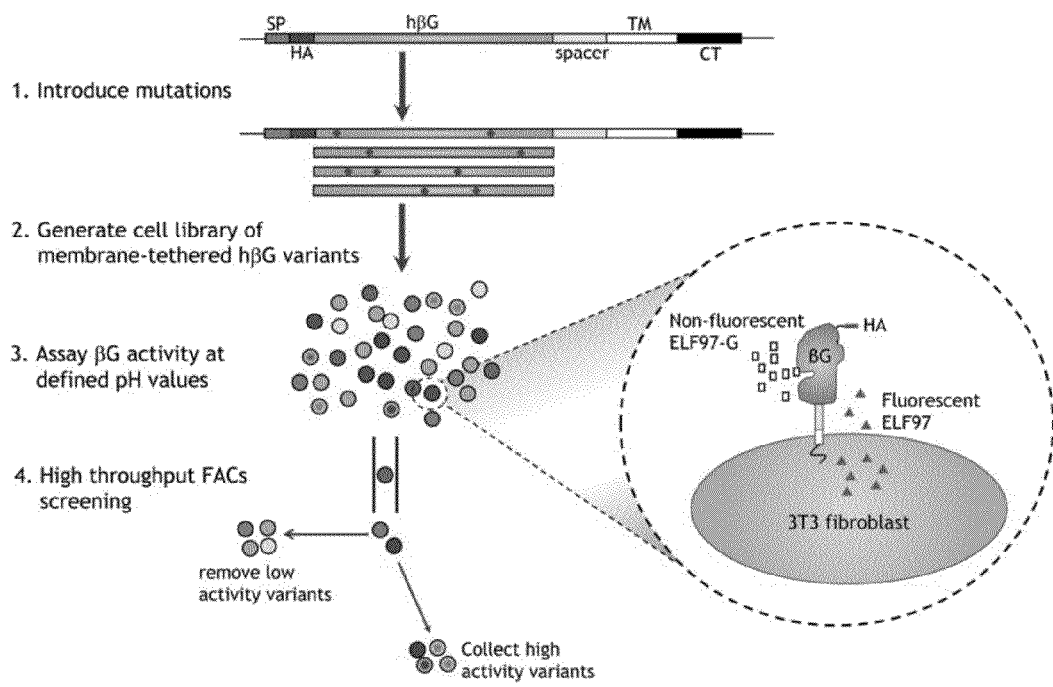
FIG. 1 is a schematic illustration depicting a screening process for identifying human beta-glucuronidase variants having high enzymatic activity at a defined pH value.

The present invention relates to human beta-glucuronidase variants having higher enzymatic activity under a physiological condition as compared to its wild-type counterpart, uses thereof in prodrug cancer therapy, and a method for identifying variants of an enzyme having elevated enzymatic activity under a defined condition as compared to the wild-type enzyme.

Human Beta-Glucuronidase Variants Having Elevated Enzymatic Activity

Beta-glucuronidase, a member of the glucuronidase family, catalyzes hydrolysis of glycosaminoglycans (e.g., heparan sulfate) to release the non-reducing end β-D-glucuronic acid residues. The amino acid sequence of the precursor form of human beta-glucuronidase is shown below.

Beta-glucuronidase can convert glucuronide prodrugs to active drugs. However, as an acid hydrolase, its activity is low at neutral pH, hindering its therapeutic application.

Disclosed herein are human beta-glucuronidase variants having elevated enzymatic activity at physiological pH, as compared to the wild-type enzyme. Listed below are the DNA and amino acid sequences of five examples (mature form):

DNA Sequences:

E1-S
(SEQ ID NO: 1)
ggggcccagccggccctgcagggcgggatgctgtaccccccaggagagccc gtcgcgggagtgcaaggagctggacggcctctggagcttccgcgccgact tctctgacaaccgacgccggggcttcgaggagcagtggtaccggcggccg ctgtgggagtcaggccccaccgtggacatgccagttccctccagcttcaa tgacatcagccaggactggcgtctgcggcattttgtcggctgggtgtggt acgaacgggaggtgatcctgccggagcgatggacccaggacctgcgcaca agagtggtgctgaggattggcagtgcccattcctatgccatcgtgtgggt gaatggggtggacacgctagagcatgaggggggctacctcccccttcgagg ccgacatcagcaacctggtccaggtggggcccctgccctcccggctccga atcactatcgccatcaacaacacactcaccccaccaccctgccaccagg gaccatccaatacctgactgacacctccaagtatcccaagggttactttg tccagaacacatattttgactttttcaactacgctggactgcagcggtct gtacttctgtacacgacacccaccacctacatcgatgacatcaccgtcac caccagcgtggagcaagacagtgggctggtgaattaccagatctctgtca agggcagtaacctgttcaagttggaagtgcgtcttttggatgcagaaaac aaagtcgtggcgaatgggactgggacccagggccaacttaaggtgccagg tgtcagcctctggtggccgtacctgatgcacgaacgccctgcctatctgt attcattggaggtgcagctgactgcacagacgtcactgggcctgtgtct gacttctacacactccctgtggggatccgcactgtggctgtcaccaagag ccagttcctcatcaatgggaaaccttctatttccacggtgtcaacaagc atgaggatgcggacatccgagggaagggcttcgactggccgctgctggtg Human beta-glucuronidase (wild-type, SEQ ID NO: 11)
  1 margsavawa algpllwgca lglqggmlyp qespsrecke ldglwsfrad fsdnrrrgfe 61 eqwyrrplwe sgptvdmpvp ssfndisqdw rlrhfvgwvw yerevilper wtqdlrtrvv 121 lrigsahsya ivwvngvdtl eheggylpfe adisnlvqvg plpsrlriti ainntltptt 181 lppgtiqylt dtskypkgyf vqntyfdffn yaglqrsvll yttpttyidd itvttsveqd 241 sglvnyqisv kgsnlfklev rlldaenkvv angtgtqgql kvpgvslwwp ylmherpayl 301 yslevqltaq tslgpvsdfy tlpvgirtva vtksqfling kpfyfhgvnk hedadirgkg 361 fdwpllvkdf nhlrwlgana frtshypyae evmqmcdryg ivvidecpgv glalpqffnn 421 vslhhhmqvm eevvrrdknh pavvmwsvan epashlesag yylkmviaht ksldpsrpvt 481 fvsnsnyaad kgapyvdvic lnsyyswyhd yghleliqlq latqfenwyk kyqkpiiqse 541 ygaetiagfh qdpplmftee yqkslleqyh lgldqkrrky vvgeliwnfa dfmteqsptr 601 vlgnkkgift rqrqpksaaf llrerywkia netryphsva ksqclenspf t -continued aaggacttcaacctgcttcgctggcttggtgccaacgctttccgtaccag ccactacccctatgcagaggaagtgatgcagatgtgtgaccgctatggga ttgtggtcatcgatgagtgtcccggcgtgggcctggcgctgccgcagttc ttcaacaacgtttctctgcatcaccacatgcaggtgatggaagaagtggt gcgtagggacaagaaccaccccgcggtcgtgatgtggtctgtggccaacg agcctgcgtcccacctagaatctgctggctactacttgaagatggtgatc gctcacaccaaatccttggaccccctcccggcctgtgacctttgtgagcaa ctctaactatgcagcagacaaggggctccgtatgtggatgtgatctgtt tgaacagctactactcttggtatcacgactacgggcacctggagttgatt cagctgcagctggccacccagtttgagaactggtataagaagtatcagaa gcccattattcagagcgagtatggagcagaaTcgattgcagggtttcacc aggatccacctctgatgttcactgaagagtaccagaaaagtctgctagag cagtaccatctgggtctggatcaaaaacgcagaaaatatgtggttggaga gctcatttggaattttgccgatttcatgactgaacagtcaccgacgagag tgctggggaataaaaagggatcttcactcggcagagacaaccaaaaagt gcagcgttccttttgcgagagagatactggaagattgccaatgaaaccag gtatccccactcagtagccaagtcacaatgtttggaaaacagcccgttta cttccgtcgac

E1-G (SEQ ID NO: 2)
ggggcccagccggccctgcagggcgggatgctgtaccccaggagagccc gtcgcgggagtgcaaggagctggacggcctctggagcttccgcgccgact tctctgacaaccgacgccggggcttcgaggagcagtggtaccggcggccg ctgtgggagtcaggccccaccgtggacatgccagttccctccagcttcaa tgacatcagccaggactggcgtctgcggcattttgtcggctgggtgtggt acgaacgggaggtgatcctgccggagcgatggacccaggacctgcgcaca agagtggtgctgaggattggcagtgcccattcctatgccatcgtgtgggt gaatggggtggacacgctagagcatgagggggctacctcccccttcgagg ccgacatcagcaacctggtccaggtggggcccctgccctcccggctccga atcactatcgccatcaacaacacactcaccccccaccaccctgccaccagg gaccatccaatacctgactgacacctccaagtatcccaagggttactttg tccagaacacatattttgacttttcaactacgctggactgcagcggtct gtacttctgtacacgacacccaccacctacatcgatgacatcaccgtcac caccagcgtggagcaagacagtgggctggtgaattaccagatctctgtca agggcagtaacctgttcaagttggaagtgcgtctttggatgcagaaaac aaagtcgtggcgaatgggactgggacccagggccaacttaaggtgccagg tgtcagcctctggtggccgtacctgatgcacgaacgccctgcctatctgt attcattggaggtgcagctgactgcacagacgtcactggggcctgtgtct gacttctacacactccctgtggggatccgcactgtggctgtcaccaagag ccagttcctcatcaatgggaaaccttctatttccacggtgtcaacaagc atgaggatgcggacatccgagggaagggcttcgactggccgctgctggtg aaggacttcaacctgcttcgctggcttggtgccaacgctttccgtaccag ccactacccctatgcagaggaagtgatgcagatgtgtgaccgctatggga ttgtggtcatcgatgagtgtcccggcgtgggcctggcgctgccgcagttc ttcaacaacgtttctctgcatcaccacatgcaggtgatggaagaagtggt gcgtagggacaagaaccaccccgcggtcgtgatgtggtctgtggccaacg agcctgcgtcccacctagaatctgctggctactacttgaagatggtgatc gctcacaccaaatccttggaccccctcccggcctgtgacctttgtgagcaa ctctaactatgcagcagacaaggggctccgtatgtggatgtgatctgtt tgaacagctactactcttggtatcacgactacgggcacctggagttgatt cagctgcagctggccacccagtttgagaactggtataagaagtatcagaa gcccattattcagagcgagtatggagcagaaGGCattgcagggtttcacc aggatccacctctgatgttcactgaagagtaccagaaaagtctgctagag cagtaccatctgggtctggatcaaaaacgcagaaaatatgtggttggaga gctcatttggaattttgccgatttcatgactgaacagtcaccgacgagag tgctggggaataaaaagggatcttcactcggcagagacaaccaaaaagt gcagcgttccttttgcgagagagatactggaagattgccaatgaaaccag gtatccccactcagtagccaagtcacaatgtttggaaaacagcccgttta cttccgtcgac

S2

(SEQ ID NO: 3)
gcggcccagccggccctgcagggcgggatgctgtaccccaggagagccc gtcgcgggagtgcaaggagctggacggcctctggagcttccgcgccgact tctctgacaaccgacgccggggcttcgaggagcagtggtaccggcggccg ctgtgggagtcaggccccaccgtggacatgccagttccctccagcttcaa tgacatcagccaggactggcgtctgcggcattttgtcggctgggtgtggt acgaacgggaggtgatcctgccggagcgatggacccaggacctgcgcaca agagtggtgctgaggattggcagtgcccattcctatgccatcgtgtgggt gaatggggtggacacgctagagcatgagggggctacctcccccttcgagg ccgacatcagcaacctggtccagAtggggcccctgccctcccggctccga atcactatcgccatcaacaacacactcaccccccaccaccctgccaccagg gaccatccaatacctgactgacacctccaagtatcccaagggttactttg tccagaacacatattttgacttttcaactacgctggactgcagcggtct gtacttctgtacacgacacccaccacctacatcgatgacatcaccgtcac caccagcgtggagcaagacagtgggctggtgaattaccagatctctgtca agggcagtaacctgttcaagttggaagtgcgtctttggatgcagaaaac aaagtcgtggcgaatgggactgggacccagggccaacttaaggtgccagg tgtcagcctctggtggccgtacctgatgcacgaacgccctgcctatctgt attcattggaggtgcagctgactgcacagacgtcactggggcctgtgtct gacttctacacactccctgtggggatccgcactgtggctgtcaccaagag ccagttcctcatcaatgggaaaccttctatttccacggtgtcaacaagc atgaggatgcggacatccgagggaagggcttcgactggccgctgctggtg aaggacttcaacctgcttcgctggcttggtgccaacgctttccgtaccag -continued ccactacccctatgcagaggaagtgatgcagatgtgtgaccgctatggga ttgtggtcatcgatgagtgtcccggcgtgggcctggcgctgccgcagttc ttcaacaacgtttctctgcatcaccacatgcaggtgatggaagaagtggt gcgtagggacaagaaccaccccgcggtcgtgatgtggtctgtggccaacg agcctgcgtcccacctagaatctgctggctactacttgaagatggtgatc gctcacaccaaatccttggacccctcccggcctgtgacctttgtgagcaa ctctaactatgcagcagacaagggggctccgtatgtggatgtgatctgtt tgaacagctactactcttggtatcacgactacgggcacctggagttgatt cagctgcagctggccacccagtttgagaactggtataagaagtatcagaa gcccattattcagagcgagtatggagcagaaTcgattgcagggtttcacc aggatccacctctgatgttcactgaagagtaccagaaaagtctgctagag cagtaccatctgggtctggatcaaaaacgcagaaaatatgtggttggaga gctcatttggaattttgccgatttcatgactTTGcagtcaccgTTgagag tgctggggaataaaaaggggatcttcactcggcagagacaaccaaaaagt gcagcgttccttttgcgagagagatactggaagattgccaatgaaaccag gtatccccactcagtagccaagtcacaatgtttggaaaacagcccgttta cttccgtcgac S28
(SEQ ID NO: 4)
gcggcccagccggccctgcagggcgggatgctgtaccccccaggagagccc gtcgcgggagtgcaaggagctggacggcctctggagcttccgcgccgact tctctgacaaccgacgccggggcttcgaggagcagtggtaccggcggccg ctgtgggagtcaggccccaccgtggacatgccagttccctccagcttcaa tgacatcagccaggactggcgtctgcggcattttgtcggctgggtgtggt acgaacgggaggtgatcctgccggagcgatggacccaggacctgcgcaca agagtggtgctgaggattggcagtgcccattcctatgccatcgtgtgggt gaatggggtggacacgctagagcatgagggggggctacctcccccttcgagg ccgacatcagcaacctggtccaggtggggcccctgccctcccggctccga atcactatcgccatcaacaacacactcaccccaccaccctgccaccagg gaccatccaatacctgactgacacctccaagtatcccaagggttactttg tccagaacacatattttgacttttttcaactacgctggactgcagcggtct gtacttctgtacacgacacccaccacctacatcgatgacatcaccgtcac caccagcgtggagcaagacagtgggctggtgaattaccagatctctgtca agggcagtaacctgttcaagttggaagtgcgtcttttggatgcagaaaac aaagtcgtggcgaatgggactgggacccagggccaacttaaggtgccagg tgtcagcctctggtggccgtacctgatgcacgaacgccctgcctatctgt attcattggaggtgcagctgactgcacagacgtcactggggcctgtgtct gacttctacacactccctgtggggatccgcactgtggctgtcaccaagag ccagttcctcatcaatgggaaacctttctatttccacggtgtcaacaagc atgaggatgcgacatccgagggaagggcttcgactggccgctgctggtg aaggacttcaacctgcttcgctggcttggtgccaacgctttccgtaccag ccactacccctatgcagaggaagtgatgcagatgtgtgaccgctatggga ttgtggtcatcgatgagtgtcccggcgtgggcctggcgctgccgcagttc ttcaacaacgtttctctgcatcaccacatgcaggtgatggaagaagtggt gcgtagggacaagaaccaccccgcggtcgtgatgtggtctgtggccaacg agcctgcgtcccacctagaatctgctggctactacttgaagatggtgatc gctcacaccaaatccttggacccctcccggcctgtgacctttgtgagcaa ctctaactatgcagcagacaagggggctccgtatgtggatgtgatctgtt tgaacagctactactcttggtatcacgactacgggcacctggagttgatt cGgctgcagctggccacccagtttgagaactggtataagaagtatcagaa gcccattattcagagcgagtatggagcagaaTcgattgcagggtttcacc aggatccacctctgatgttcactgaagagtaccagaaaagtctgctagag cagtaccatctgggtctggatcaaaaacgcagaaaatatgtggttggaga gctcatttggaattttgccgatttcatgactTaCcagtcaccgTTCagag tgctggggaataaaaaggggatcttcactcggcagagacaaccaaaaagt gcagcgttccttttgcgagagagatactggaagattgccaatgaaaccag gtatccccactcagtagccaagtcacaatgtttggaaaacagcccgttta cttccgtcgac E2-20
(SEQ ID NO: 5)
gcggcccagccggccctgcagggcgggatgctgtaccccccaggagagccc gtcgcgggagtgcaaggagctggacggcctctggagcttccgcgccgact tctctgacaaccgacgccggggcttcgaggagcagtggtaccggcggccg ctgtgggagtcaggccccaccgtggacatgccagttccctccagcttcaa tgacatcagccaggactggcgtctgcggcattttgtcggctgggtgtggt acgaacgggaggtgatcctgccggagcgatggacccaggacctgcgcaca agagtggtgctgaggattggcagtgcccattcctatgccatcgtgtgggt gaatggggtggacacgctagagcatgagggggggctacctcccccttcgagg ccgacatcagcaacctggtccaggtggggcccctgccctcccggctccga atcactatcgccatcaacaacacactcaccccaccaccctgccaccagg gaccatccaatacctgactgacacctccaagtatcccaagggttactttg tccagaacacatattttgacttttttcaactacgctggactgcagcggtct gtacttctgtacacgacacccaccacctacatcgatgacatcaccgtcac caccagcgtggagcaagacagtgggcAggtgaattaccagatctctgtca agggcagtaaccAgttcaagttggaagtgcgtcttttagatgcagaaaac aaagtcgtggcgaatgggactgggacccagggccaacttaaggtgccagg tgtcagcctctggtggccgtacctgatgcacgaacgccctgcctatctgt attcattggaggtgcagctgactgcacagacgtcactggggcctgtgtct gacttctacacactccctgtggggatccgcactgtggctgtcaccaagag ccagttcctcatcaatgggaaacctttctatttccacggtgtcaacaagc atgaggatgcgacatccgagggaagggcttcgactggccgctgctggtg aaggacttcaacctgcttcgctggcttggtgccaacgctttccgtaccag ccactacccctatgcagaggaagtgatgcagatgtgtgaccgctatggga -continued ttgtggtcatcgatgagtgtcccggcgtgggcctggcgctgccgcagttc ttcaacaacgtttctctgcatcaccacatgcaggtgatggaagaagtgg gcgtagggacaagaaccaccccgcggtcgtgatgtggtctgtggccaacg agcctgctcccacctagaatctgctggctactacttgaagatggtgatc gctcacaccaaatccttggacccctcccggcctgtgacctttgtgagcaa ctctaactatgcagcagacaagggggctccgtatgtggatgtgatctgtt tgaacagctactactcttggtatcacgactacgggcacctggagttgatt cagctgcagctggccacccagtttgagaactggtataagaagtatcagaa gcccattattcagagcgagtatggagcagaaGGCattgcagggtttcacc aggatccacctctgatgttcactgaagagtaccagaaaagtctgctagag cagtaccatctgggtctggatcaaaaacgcagaaaatatgtggttggaga gctcatttggaattttgccgatttcatgactgaacagtcaccgacgagag tgctggggaataaaaaggggatcttcactcggcagagacaaccaaaaagt gcagcgttcctttt gcgagagagatactggaagattgccaatgaaaccag gtatccccactcagtagccaagtcacaatgtttggaaaacagcccgttta cttccgtcgac Amino Acid Sequences E1-S
(SEQ ID NO: 6)
gaqpalqggmlypqespsreckeldglwsfradfsdnrrrgfeeqwyrrp lwesgptvdmpvpssfndisqdwrlrhfvgwvwyerevilperwtqdlrt rvvlrigsahsyaivwvngvdtleheggylpfeadisnlvqvgplpsrlr itiainntltpttlppgtiqyltdtskypkgyfvqntyfdffnyaglqrs vllyttpttyidditvttsveqdsglvnyqisvkgsnlfklevrlldaen kvvangtgtqgqlkvpgvslwwpylmherpaylyslevqltaqtslgpvs dfytlpvgirtvavtksqflingkpfyfhgvnkhedadirgkgfdwpllv kdfnllrwlganafrtshypyaeevmqmcdrygivvidecpgvglalpqf fnnvslhhhmqvmeevvrrdknhpavvmwsvanepashlesagyylkmvi ahtksldpsrpvtfvsnsnyaadkgapyvdviclnsyyswyhdyghleli qlqlatqfenwykkyqkpiiqseygaesiagfhqdpplmfteeyqkslle qyhlgldqkrrkyvvgeliwnfadfmteqsptrvlgnkkgiftrqrqpks aafllrerywkianetryphsvaksqclenspftsvd E1-G
(SEQ ID NO: 7)
gaqpalqggmlypqespsreckeldglwsfradfsdnrrrgfeeqwyrrp lwesgptvdmpvpssfndisqdwrlrhfvgwvwyerevilperwtqdlrt rvvlrigsahsyaivwvngvdtleheggylpfeadisnlvqvgplpsrlr itiainntltpttlppgtiqyltdtskypkgyfvqntyfdffnyaglqrs vllyttpttyidditvttsveqdsglvnyqisvkgsnlfklevrlldaen kvvangtgtqgqlkvpgvslwwpylmherpaylyslevqltaqtslgpvs dfytlpvgirtvavtksqflingkpfyfhgvnkhedadirgkgfdwpllv kdfnllrwlganafrtshypyaeevmqmcdrygivvidecpgvglalpqf fnnvslhhhmqvmeevvrrdknhpavvmwsvanepashlesagyylkmvi ahtksldpsrpvtfvsnsnyaadkgapyvdviclnsyyswyhdyghleli qlqlatqfenwykkyqkpiiqseygaegiagfhqdpplmfteeyqkslle qyhlgldqkrrkyvvgeliwnfadfmteqsptrvlgnkkgiftrqrqpks aafllrerywkianetryphsvaksqclenspftsvd S2
(SEQ ID NO: 8)
aaqpalqggmlypqespsreckeldglwsfradfsdnrrrgfeeqwyrrp lwesgptvdmpvpssfndisqdwrlrhfvgwvwyerevilperwtqdlrt rvvlrigsahsyaivwvngvdtleheggylpfeadisnlvqmgplpsrlr itiainntltpttlppgtiqyltdtskypkgyfvqntyfdffnyaglqrs vllyttpttyidditvttsveqdsglvnyqisvkgsnlfklevrlldaen kvvangtgtqgqlkvpgvslwwpylmherpaylyslevqltaqtslgpvs dfytlpvgirtvavtksqflingkpfyfhgvnkhedadirgkgfdwpllv kdfnllrwlganafrtshypyaeevmqmcdrygivvidecpgvglalpqf fnnvslhhhmqvmeevvrrdknhpavvmwsvanepashlesagyylkmvi ahtksldpsrpvtfvsnsnyaadkgapyvdviclnsyyswyhdyghleli qlqlatqfenwykkyqkpiiqseygaesiagfhqdpplmfteeyqkslle qyhlgldqkrrkyvvgeliwnfadfmtlqsplrvlgnkkgiftrqrqpks aafllrerywkianetryphsvaksqclenspftsvd S28
(SEQ ID NO: 9)
aaqpalqggmlypqespsreckeldglwsfradfsdnrrrgfeeqwyrrp lwesgptvdmpvpssfndisqdwrlrhfvgwvwyerevilperwtqdlrt rvvlrigsahsyaivwvngvdtleheggylpfeadisnlvqvgplpsrlr itiainntltpttlppgtiqyltdtskypkgyfvqntyfdffnyaglqrs vllyttpttyidditvttsveqdsglvnyqisvkgsnlfklevrlldaen kvvangtgtqgqlkvpgvslwwpylmherpaylyslevqltaqtslgpvs dfytlpvgirtvavtksqflingkpfyfhgvnkhedadirgkgfdwpllv kdfnllrwlganafrtshypyaeevmqmcdrygivvidecpgvglalpqf fnnvslhhhmqvmeevvrrdknhpavvmwsvanepashlesagyylkmvi ahtksldpsrpvtfvsnsnyaadkgapyvdviclnsyyswyhdyghleli rlqlatqfenwykkyqkpiiqseygaesiagfhqdpplmfteeyqkslle qyhlgldqkrrkyvvgeliwnfadfmtyqspfrvlgnkkgiftrqrqpks aafllrerywkianetryphsvaksqclenspftsvd E2-20
(SEQ ID NO: 10)
Aaqpalqggmlypqespsreckeldglwsfradfsdnrrrgfeeqwyrrp lwesgptvdmpvpssfndisqdwrlrhfvgwvwyerevilperwtqdlrt rvvlrigsahsyaivwvngvdtleheggylpfeadisnlvqvgplpsrlr itiainntltpttlppgtiqyltdtskypkgyfvqntyfdffnyaglqrs vllyttpttyidditvttsveqdsgqvnyqisvkgsnqfklevrlldaen kvvangtgtqgqlkvpgvslwwpylmherpaylyslevqltaqtslgpvs -continued

```
dfytlpvgirtvavtksqflingkpfyfhgvnkhedadirgkgfdwpllv kdfnllrwlganafrtshypyaeevmqmcdrygivvidecpgvglalpqf fnnvslhhhmqvmeevvrrdknhpavvmwsvanepashlesagyylkmvi ahtksldpsrpvtfvsnsnyaadkgapyvdviclnsyyswyhdyghleli qlqlatqfenwykkyqkpiiqseygaegiagfhqdpplmfteeyqkslle qyhlgldqkrrkyvvgeliwnfadfmteqsptrvlgnkkgiftrqrqpks aafllrerywkianetryphsvaksqclenspftsvd
```

Also disclosed herein are beta-glucuronidase variants that share high sequence identity (e.g., at least 95%, 97%, or 99%) to any of SEQ ID NOs:6-10. The "percent identity" of two amino acid sequences is determined using the algorithm of Karlin and Altschul *Proc. Natl. Acad. Sci.* USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

The beta-glucuronidase variants described in the preceding paragraph can be prepared by introducing one or more mutations (e.g., single amino acid substitutions) in one of SEQ ID NOs: 6-10 at a certain position(s), particularly at a position(s) that corresponds to 159, 243, 255, 518, 545, 595, and 599 in wild-type human beta-glucuronidase (SEQ ID NO:11). In another example, a hydrophobic amino acid is introduced in the position corresponding to 599 in SEQ ID NO:11. In another example, a neutral or positively-charged amino acid is introduced in the position corresponding to 595 in SEQ ID NO:11.

Any of the beta-glucuronidase variants described above can be prepared by a conventional method, e.g., recombinant technology. Their enzymatic activity under a particular condition (e.g., a physiological condition) can be determined following routine procedures, such as the method described in Example 1 below.

Application of Human Beta-Glucuronidase Variants in Prodrug Anti-Cancer Therapy

Under a physiological condition (e.g., neutral pH), the human beta-glucuronidase variants described above are more active than the wild-type enzyme in converting a glucuronide prodrug to an active drug. They therefore are preferable enzymes for use in prodrug therapy. To perform beta-glucuronidase prodrug therapy, the enzyme can be delivered to cancer cells via, e.g., cancer-targeting-agent-directed or gene-directed approaches, so as to convert an anti-cancer glucuronide prodrug to an active drug at tumor sites. This glucuronidase variant-mediated prodrug therapy can be applied for treating any types of cancer, depending upon the prodrug used in the therapy.

(i) Cancer-Targeting-Agent-Directed Enzyme Prodrug Therapy

In this approach, a beta-glucuronidase variant is delivered to cancer sites via fusion with a protein-based cancer target agent to form a fusion protein or conjugation with a cancer-targeting agent to form a conjugate. The fusion protein can be prepared by traditional recombinant technology. To prepare the conjugate, the beta-glucuronidase variant can be associated with a cancer target agent either directly or through a linker (e.g., a crosslinking agent) or a carrier (e.g., micelle) via covalent or non-covalent bonds.

A cancer target agent is a compound, either a macromolecule or a small molecule, capable of specifically binding to cancer cells. Protein-based cancer targeting agents include, but are not limited to, single-chain antibodies specific to tumor antigens and peptides specific to cancer cell surface receptors. Any cancer-targeting single-chain antibodies known in the art can be used in this therapy. Examples include, but are not limited to, CC49, PR1A3, A3, CC7, 4D5MOC-B, WX-G250, CP-751,871, J591, CNTO 95, Hu14.18, IMC-A12, L19, TRM-1, 7.6.3, and trastuzumab (HERCEPTIN ®). See Yang et al., Cancer Research 59:1236-1243 (1999); Willuda et al., Cancer Research 59:5758-5767 (1999); Tarli et al., Blood 94:192-198 (1999); Cohen et al., Clinical Cancer Research 11:2063-2073 (2005); Bleumer et al., British J. Cancer 90:985-990 (2004); Yoon et al., J. Biol. Chem. 281:6985-6992 (2006); Vogel et al., J. Clinical Oncology 20:719-726 (2002); Cutsem et al., J. Clinical Oncology 25:1658-1664 (2007); Tolcher et al., J. Clinical Oncology 25:1390-1395 (2007); Osenga et al., Clin. Cancer Res. 12(6): 1750-1759 (2006); Mullamitha et al., Clin. Cancer Res. 13(7):2128-2135 (2007); Milowsky et al., J. Clinical Oncology 25(5):540-547 (2007); Rowinsky et al., Clin. Cancer Res. 13(18 Suppl):5549s-5555s (2007); and Stewart et al., Cancer Immunol. Immunother 47:299-306 (1999). Exemplary cancer-targeting peptides include, but are not limited to, AHNP, RGD4C, HN-1, CSNRDARRC, (SEQ ID NO: 12), CNGRCVSGCAGRC, (SEQ ID NO: 13), $Z_{HER2:342\text{-}pep2}$, ZEGFR:1907, and SP94. See Lo et al., Mol. Cancer. Ther. 7(3):579-589 (2008); Pasqualini et al., Cancer Res. 60:722-727 (2000); Tolmachev et al., J. Nucl. Med. 50:274-283 (2009); Orlova et al., Cancer Res. 67(5):2178-2186 (2007); Line et al., J. Nucl. Med. 46:1552-1560 (2005); Lee et al., Mol. Cancer. Res. 5(1):11-19 (2007); and Hong et al., Cancer Res. 60:6551-6556 (2000). The cancer-targeting agent also can be aptamers, such as those disclosed in Hicke et al., J. Nucl. Med. 47:668-678 (2006) and Chu et al., Cancer Res. 66(12):5989-5992 (2006).

Either the fusion protein or the conjugate described above can be co-administered to a cancer patient with an effective amount of an anti-cancer prodrug for treating cancer. The term "treating" as used herein refers to the application or administration of a composition including one or more active agents to a subject, who has a disease, a symptom of the disease, or a predisposition toward the disease, with the purpose to cure, heal, alleviate, relieve, alter, remedy, ameliorate, improve, or affect the disease, the symptoms of the disease, or the predisposition toward the disease. "An effective amount" as used herein refers to the amount of each active agent required to confer therapeutic effect on the subject, either alone or in combination with one or more other active agents. Effective amounts vary, as recognized by those skilled in the art, depending on route of administration, excipient usage, and co-usage with other active agents.

The anti-cancer prodrug can be a glucuronide prodrug or a compound (e.g., CPT-11, epirubicin, teniposide, flavopiridol, and etoposide) that converts to a glucuronide prodrug metabolically. Such prodrugs are well known in the art. See, e.g., Prijovich et al., Cancer Chemother Pharmacol. 60:7-17 (2007); Prijovich et al., British J. Cancer 86:1634-1638 (2002); Juan et al., Clin. Cancer Res. 15(14):4600-4611; Houba et al., Biochemical Pharmacology 57:673-680 (1999);

Cheng et al., Cancer Gene Therapy 15:393-401 (2008); Chen et al., Int. J. Cancer 94:850-858 (2001); Cheng et al., British J. Cancer 79:1378-1385 (1999); Wang et al., Cancer Res. 52:4484-4491 (1992); Graaf et al., British J. Cancer 86:811-818 (2002); Cheng et al., Cancer Gene Therapy 11:380-388 (2004); Cheng et al., Biochemical Pharmacology 58:325-328 (1999); Angenault et al., Bioorganic & Medicinal Chemistry Letters 13:947-950 (2003); Murdter et al., J. Pharmacology & Experimental Therapeutics 201:223-228 (2002); Poujol et al., Clinical Chemistry 49(11):1900-1908 (2003); Innocenti et al., Clin. Cancer Res. 6:3400 (2001); Rossi et al., Cancer Chemother Pharmacol. 13:211-214 (1984); Innocenti et al., Drug Metab. Dispos. 29:686-692 (2000); and Watanabe et al., Drug Metab Dispos 31:589-595 (2003).

The beta-glucuronidase variant-containing fusion protein or conjugate, either alone or in combination with a prodrug, can be mixed with a pharmaceutically acceptable carrier to form a pharmaceutical composition. The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form more soluble complexes with the oxadiazole compounds, or more solubilizing agents, can be utilized as pharmaceutical carriers for delivery of the oxadiazole compounds. Examples of other carriers include colloidal silicon dioxide, magnesium stearate, sodium lauryl sulfate, and D&C Yellow # 10.

To practice the therapy mentioned above, the fusion protein/conjugate is co-administered, sequentially or simultaneously, with the prodrug orally, parenterally, by inhalation spray, topically, rectally, nasally, buccally, vaginally or via an implanted reservoir. Upon administration, the cancer-target agent in the fusion protein/conjugate leads the beta-glucuronidase variant to cancer cells to convert the prodrug to its active form at cancer sites. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An oxadiazole compound-containing composition can also be administered in the form of suppositories for rectal administration.

(ii) Gene-directed Enzyme Prodrug Therapy

Alternatively, one of the beta-glucuronidase variants described above can be delivered to cancer cells via a DNA construct designed for expressing the variant in cancer cells, preferably on the surfaces of cancer cells. In this construct, the coding sequence of the variant is in operative linkage with a promoter suitable for driving gene expression in cancer cells. Methods for expressing foreign genes in cancer cells are known in the art. See, e.g., Chen et al., Proc. Natl. Acad. Sci. USA 91:3054-3057 (2004); Moolten et al., J. Natl. Cancer Inst. 82:297-300 (1990); Sung et al., Mol. Ther. 4:182-191 (2001); and Pandha et al., J. Clin. Oncol. 17:2180-2189 (1999). To achieve cell surface expression, the nucleotide sequence coding for a variant can be fused with a coding sequence for a cell membrane anchoring domain. A membrane anchoring domain contains a fragment from a cell surface protein that functions as a membrane anchor (e.g., a transmembrane domain of a cell surface receptor). In one example, the membrane anchoring domain includes the transmembrane and cytoplamic tail of antigen B7-1. Preferably, the nucleotide sequence coding for the variant is further fused at its 5' end with another nucleotide sequence that encodes a signal peptide. Alternatively, the nucleotide sequence encoding the variant is fused with, at its 5' end and 3' end respectively, a coding sequence for a signal peptide and a coding sequence for a fragment composed of hydrophobic amino acids. During protein processes through the secretory pathway, this hydrophobic amino acid fragment is replaced with glycosylphosphatidylinositol (GPI anchor), which functions as a membrane anchor.

The DNA construct can be co-administered with an anti-cancer prodrug to a cancer patient via conventional methods.

Screening Assay for Identifying Lysosomal Acid Hydrolase Variants Having Elevated Enzymatic Activity under Desired Conditions Also disclosed herein is a screening method for identifying variants of an enzyme that have elevated enzymatic activity relative to its wild-type counterpart under a desired condition (e.g., a physiological condition). In one example, variants of a lysosomal acid hydrolase suitable for use in prodrug therapy are the targets. Lysosomal acid hydrolases are digestive enzymes (e.g., glucosidases, lipases, proteases, and nucleases) located in lysosomes. Wild-type lysosomal enzymes are pH sensitive. Namely, they are active in the acidic environment inside lysosomes and function less well in the alkaline environment of the cytosol. Introducing mutations in wild-type enzymes can change their pH profile, thereby enhancing their activity under a physiological condition, such as neutral pH.

Variants of an enzyme can be identified using a mammalian cell surface display system as described below. First, a mammalian cell library for surface displaying of enzyme variants is prepared following methods known in the art. In one example, each variant is fused with a cell membrane anchoring domain as described above, which facilitates surface display of the variant. See, e.g., Chen et al., 2006. Preferably, DNA plasmids encoding the fusion proteins (preferably including a signal peptide at their N-termini) are introduced into cells by retroviral transduction at low MOI so that each transduced cell stably expresses a single copy of a variant. Next, cells in the library are examined to determine their surface enzymatic activity under a defined condition. The surface expression levels of the enzyme variants can also be determined and specific enzymatic activity of each variant can be calculated by normalizing its surface enzymatic activity against its protein level. Finally, cells displaying high enzymatic activities, particularly high specific enzymatic activities, are identified and the variants expressed therein are characterized to determine their amino acid sequences and enzymatic activity.

FIG. 1 shows an example of the screening method described above. First, a nucleotide encoding a fusion protein containing human beta-glucuronidase is constructed by recombinant technology. The fusion protein contains, from N-terminus to C-terminus, an immunoglobulin kappa chain signal peptide (SP), an HA epitope (HA), human β-glucuronidase, the first extracellular domain (spacer) of the murine B7-1 antigen, the transmembrane domain (TM) of B7-1, and the cytoplasmic tail (CT) of B7-1. Next, mutations are introduced into the human beta-glucuronidase gene by a conventional method (e.g., error-prone PCR, DNA shuffling or saturation mutagenesis) to produce a plurality of human beta-glucuronidase variants. The nucleotide sequences each encoding a variant-containing fusion protein are inserted into a suitable expression vector (e.g., a retroviral vector) and introduced into suitable mammalian host cells (e.g., 3T3 cells) to generate a cell library for surface displaying of human β-glucuronidase variants. The cells in the library are then placed under a physiological condition, such as neutral pH, and their surface beta-glucuronidase activity is examined. In one example, ELF97β-D-glucuronide is used as the substrate for determine glucuronidase activities. Beta-glucuronidase converts ELF97β-D-glucuronide to fluorescent ELF97 alcohol, which is accumulated on cell surfaces. Optionally, a dye-conjugated anti-beta-glucuronidase antibody or a dye-conjugated anti-HA antibody is used for determining surface enzyme levels and specific enzymatic activities are calculated as described above. Cells exhibiting higher beta-glucuronidase activity, indicated by high surface fluorescent levels, can be collected by, e.g., FACS, and expanded for further analysis.

In addition to screen for lysosomal acid hydralase variants having elevated enzymatic activity under a physiological condition, the above described method also can be used to identify enzyme variants that exhibit elevated enzymatic activity at an acidic pH condition. Such variants are useful in replacement therapy of patients suffering from Sly disease (mucopolysaccharidosis type VII), especially for organs, such as the brain, which are difficult to target. See Grubb et al., Proc. Natl. Aca. Sci. U.S.A. 105:2616-2621 (2008).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Identification of Human Beta-Glucuronidase Mutants with Elevated Enzymatic Activity at Neutral pH A Mammalian Cell Surface-display Enzyme Screening System (i) Construction of Mammalian Cell Lines Stably Expressing Surface Beta-Glucuronidases Each of the cDNAs encoding human and mouse beta-glucuronidases (Genbank accession no. NM_000181, 03-SEP-2009 and Genbank accession no. J02836.1, 29-APR-1996) was fused to the juxtamembrane Ig-like extracellular domain, transmembrane domain and cytoplasmic tail of murine B7-1. See Chen et al., Cancer Gene Ther 14:187-200 (2007). Mouse β-glucuronidase was employed for some assays because it displays about three-fold greater enzymatic activity than human β-glucuronidase at pH 7.0, allowing better sensitivity for initial method development.

The fusion genes, cloned into a retroviral expression vector, were introduced into GP293 cells (Clontech) together with pVSV-G plasmid (Clontech, Mountainview, Calif.) to produce recombinant retroviral particles. Two days after transfection, the culture medium was filtered, mixed with 8 mg/ml polybrene and added to BALB/3T3 fibroblasts (ATCC CCL-163), CT26 murine colon carcinoma cells (ATCC CRL-2638), or EJ human bladder carcinoma cells (see Marshall et al., J. Natl. Cancer Inst. 58:1743-51 (1977). The infected 3T3 and CT26 cells were cultured in DMEM (4.5 g/l glucose) supplemented with 10% bovine serum, 2.98 g/l HEPES, 2 g/l NaHCO$_3$, 100 U/ml penicillin, and 100 µg/ml streptomycin, as well as and 0.5 mg/ml G418 (Calbiochem, San Diego, Calif.) for selection of cell lines that stably express either human or mouse beta-glucuronidase. The infected EJ cells were cultured in RPMI containing the same supplements. The surface expression of the beta-glucuronidases was determined by surface immunofluorescence staining with FITC labeled mouse anti-hβG mAb 7G8 and rat anti-mβG mAb 7G7 (see Chen et al.). It was further determined by hydrolysis of the substrate ELF97β-D-glucuronide (Molecular Probes, Eugene, Oreg.) to ELF97 alcohol, following the method described in Telford et al., Cytometry 43:117-125 (2001). ELF97 alcohol is a fluorescent product that remained associated with cells expressing surface beta-glucuronidase.

(ii) Examination of Beta-glucuronidase Expression on Cell Surfaces

The cell surface expression of the beta-glucuronidases was confirmed by trypsin proteolysis analysis as follows. 3T3 cells that stably expressed β-glucuronidases on their surfaces were treated with 250, 125, 62.5, or 0 µg/ml trypsin for 5 min at 37° C. The levels of surface beta-glucuronidases were determined by staining with the anti-glucuronidase antibodies mentioned above and the results indicate that trypsin treatment reduced the cell surface amount of the enzymes in a dose-dependent manner.

The surface enzymatic activity was examined by mixing the trypsin-treatment or untreated cells with 100 µM ELF97 β-D-glucuronide at pH 6.0 for 15 min at 37° C. The trypsin-treated cells displayed much lower surface fluorescence as compared to the untreated cells, indicating that trypsin proteolysis reduced enzymatic activity of the beta-glucuronidases expressed on cell surfaces.

Wild-type EJ cells and EJ cells expressing HA-tagged mouse beta-glucuronidase (EJ/mβG cells) were seeded separately or mixed on cover slides and then stained with 100 µM ELF97 β-D-glucuronide to examine beta-glucuronidase activity and with biotin-labeled goat anti-HA followed by streptavidin-labeled rhodamine to examine cell surface expression of the mouse beta-glucuronidase expression. Cells were observed under a fluorescence microscope equipped with a CCD detector. Results thus obtained show that EJ/mβG cells were clearly distinguishable from the wild-type cells under fluorescence illumination after staining mixed cell populations with ELF97 β-D-glucuronide.

CT26/mβG cells were stained with 25 μM ELF97 β-D-glucuronide at pH 6.0 or pH 7.0 for 5 min at room temperature. Negative control CT26 cells were stained with ELF97 β-D-glucuronide at pH 6. The cells stained at pH 7.0 exhibited much higher fluorescence intensity than those stained at pH 6.0, indicating that their enzymatic activity depended on the extracellular pH.

To determine if high-throughput flow cytometric sorting of cells based on relative beta-glucuronidase activity was feasible, wild-type CT26 cells, CT26/mβG cells, or a mixture thereof (50/50) were first stained with rat anti-mβG antibody followed by goat anti-rat FITC conjugate and then incubated with ELF97 β-D-glucuronide, pH 6.0 at room temperature for 5 minutes. Upon FACS analysis, two discrete populations of cells were observed, demonstrating that enzymatically-generated ELF97 alcohol remained associated with cells expressing membrane-bound beta-glucuronidase during the staining and analysis procedure.

cDNA Libraries for Surface Expression of Human Beta-Glucuronidase Variants (i) Generating Human Beta-glucuronidase Variant cDNA Library Via Error-prone PCR A silent mutation was made to change cytosine to guanidine at position 411 of the human β-glucuronidase gene in pLNCX-hβG-eB7, which is described in Chen et al., 2007, to remove an internal Sal I site. The resulting vector, pLNCX-hβGs-eB7, was employed as a template for error-prone PCR following the method described in Cadwell et al., PCR methods Appl 2:28-33 (1992), using primers P1 (5'-TAT GCT GG *G GCC CAG CCG GCC* -3', (SEQ ID NO: 14), which contains part of the HA epitope at the 5' end and a Sfi I restriction site at the 3' end as highlighted in boldface) and P2 (5'-CTG AGA TGA GTT TTT GTT C *GT CGA C* -3' (SEQ ID NO: 15), which contains part of the myc epitope at the 5' end and a Sal I restriction site at the 3' end also highlighted in boldface). A mutagenic buffer containing 8 mM dCTP, 8 mM dTTP, 48 mM MgCl$_2$, and 5 mM MnCl$_2$ (Matsumura and Ellington, 2001) was added (1.25 or 2.5 μl) to each 50 μl PCR reaction using 5 units Taq polymerase (Takara, Shiga, Japan) for amplification. The PCR product was digested with Sfi I and Sal I enzymes, ligated into pLNCX-hβGs-eB7, which was digested with the same enzymes, and introduced into DH5α competent cells by electroporation. Transformed bacteria were selected on 15 cm carbenicillin-containing LB agar plates for 16 hours at 37° C. Colonies from multiple plates were collected and expanded in carbenicillin-containing LB medium and then amplified by addition of 170 μg/ml chloramphenicol. Plasmid DNAs from the transformed bacteria were purified by centrifugation in a CsCl-ethidium bromide density gradient at 60,000 rpm in a Ti 70.1 rotor at 4° C. for 24 hours using a Beckman Optima L-90K ultracentrifuge (Beckman Coulter, Fullerton, Calif.). The plasmid DNAs thus obtained were co-introduced into GP293 cells with plasmid pVSV-G plasmid to produce recombinant retroviral particles. Two days after transfection, the culture medium was filtered, mixed with 8 mg/ml polybrene. 3T3 cells were infected with the viral particles at low MOI (multiplicity of infection, ~0.6 cfu/cell) with a VSV-G pseudotyped retroviral virus library to generate ~$10^7$ independent 3T3 clones. The resultant human beta-glucuronidase variant 3T3 library (EP1 library) has a diversity of ~$5 \times 10^6$ containing an average of 4.5 amino acid mutations per human β-glucuronidase gene.

(ii) Generating Human Beta-glucuronidase Variant cDNA Library Via Saturation Mutagenesis To generate randomized mutations at amino acid positions 545, 595, and 599 in human β-glucuronidase, two rounds of site-directed mutagenesis were performed to introduce the desired mutations in the human β-glucuronidase gene using the QuickChange® site-directed mutagenesis kit (Stratagene, La Jolla, Calif.). All possible amino acids were introduced at amino acid position 545 with primers P3 (5'-CGA GTA TGG AGC AGA ANN SAT TGC AGG GTT TCA CCA GGA TCC-3') (SEQ ID NO: 16), and P4 (5'-GGA TCC TGG TGA AAC CCT GCA ATS NNT TCT GCT CCA TAC TCG-3') (SEQ ID NO: 17), where N represents G, A, T or C, and S represents G or C. A second round of site-directed mutagenesis was performed with primers P5 (5'-GGA ATT TTG CCG ATT TCA TGA CTN NSC AGT CAC CGN NSA GAG TGC TGG GGA ATA AAA AGG GG-3') (SEQ ID NO: 18), and P6 (5'-CCC CTT TTT ATT CC CAG CAC TCT SNN CGG TGA CTG SNN AGT CAT GAA ATC GGC AAA ATT CC-3') (SEQ ID NO: 19), to further introduce all possible amino acids at positions 595 and 599 of human β-glucuronidase genes. The resultant PCR products were ligated into the Sfi I and Sal I sites present in pLNCX-hβGs-eB7 and a new 3T3 cell library was generated following the method described above.

E1-G (50%) and E1-A (50%) variants, having the amino acid residue at position 545 (T) being replaced with G or A, were employed as starting material to generate a new error-prone cDNA library (EP2) with $5 \times 10^6$ members containing an average of 2.6 amino acid mutations per human β-glucuronidase gene.

(iii) Generating a Human Beta-glucuronidase Variant cDNA Library Via DNA Shuffling The cells in the libraries mentioned above were subjected to FACS analysis to enrich those that express human beta-glucuronidase variants with high enzymatic activity, following the method described below. Variant human β-glucuronidase genes were recovered from the enriched 3T3 cells by RT-PCR. Human β-glucuronidase DNA (1 μg) was digested with 0.025 U of DNase I (Takara, Shiga, Japan) in 25 μl of 50 mM Tris-HCl, pH 7.4, 1 mM MgCl$_2$ for 11 minutes at 25° C. The reaction was quenched by adding 5 μl of 0.5 M EDTA. DNA fragments ranging from 100-300 bases on a 1% agarose gel were reassembled in 35 cycles of primerless PCR, as described in Stemmer, Nature 370:389-391 (1994). The full length recombinant products, amplified in a standard PCR reaction with the P1 and P2 primers described above, were cloned in pLNCX-hβGs-eB7 to create a new 3T3 cell library.

(iv) Selecting Mammalian Cells Expressing Human Beta-glucuronidase Variants with Elevated Enzymatic Activity at Particular pH Values The 3T3 cell libraries mentioned above were screened by FACS analysis for cells that express human β-glucuronidase variants with elevated enzymatic activity. $10^7$ 3T3 cells expressing membrane-bound human β-glucuronidase variants were washed and suspended in 0.4 ml BSA/HBSS (5.4 mM KCl, 0.3 mM Na$_2$HPO$_4$, 0.4 mM KH$_2$PO$_4$, 4.2 mM NaHCO$_3$, 1.3 mM CaCl$_2$, 0.5 mM MgCl$_2$, 0.6 mM MgSO$_4$, 137 mM NaCl, 5.6 mM D-glucose, pH 7.4) containing 0.5% bovine serum albumin (BSA) and 20 μg/ml 7G8-FITC for 30 min at 4° C. Cells were then washed and incubated with 25, 50 or 100 μM ELF97 β-D-glucuronide at defined pH values in 50 mM Bis-Tris, 25 mM glucose, 85.6 mM NaCl, 5.4 mM KCl, 0.6 mM MgSO$_4$, 1.3 mM CaCl$_2$) at 37° C. for 10 min. The cells were washed with ice-cold 0.5% BSA/HBSS and suspended in 0.5% BSA/HBSS containing 5 µg/ml propidium iodide (Sigma). Cells were then sorted on a FACSVantage DiVa (Becton, Dickinson and Company, Franklin Lakes, N.J.) equipped with an Enterprise IIC argon laser for dual excitation at 488 and 351-364 nm. Dead cells (propidium iodide positive, high FL3 fluorescence) were gated out before 7G8-FITC immunofluorescence was detected at excitation/emission wavelengths of 488/515 nm (FL1) and ELF97 was detected at excitation/emission wavelengths of 351/530 nm (FL4). In some experiments, cells were sorted twice each round: those exhibiting the highest 10% activity were collected and then immediately sorted again to collect the cells displaying the highest 5% activity (representing 0.5% of the total starting population). This double sorting process greatly decreased contamination with low activity cells. The sorted cells were cultured for 4-10 days for sequential rounds of cell sorting or RNA extraction. Flow cytometer data was analyzed using Flowjo (Tree star, Ashland, Oreg.).

Following the procedure described above, cells in the 3T3 library prepared via error-prone PCR, as described in section (i) above, were selection by G418. Viable cells were stained with the 7G8-FITC antibody and incubated with ELF97 β-D-glucuronide. Afterwards, the stained cells were sorted on a flow cytometer to collect cells expressing beta-glucuronidase variants with enhanced enzymatic activity relative to the protein expression levels. The first round of screening was performed at pH 5.0 to enrich for rare cells displaying enhanced O-glucuronidase enzymatic activity at this pH (slighted higher than its optimal pH). Selected cells (~0.5% of the total cell population) were cultured to expand their numbers and then resorted two additional times after immunofluorescence staining for human β-glucuronidase expression with 7G8-FITC and labeling β-glucuronidase activity with ELF97 β-D-glucuronide at pH 6.5 to isolate cells displaying enhanced surface enzymatic activity at this elevated pH. The sorted population displayed increased enzymatic activity as compared to cells expressing membrane-bound wild-type human β-glucuronidase. The sorted population also exhibited enhanced enzyme activity at both pH 5.0 and pH 6.5, indicating that enzyme variants with a broader pH profile can be isolated by applying selection pressure based on reaction pH.

DNA plasmids were extracted from 12 individual cell clones and subjected to DNA sequencing to examine mutations in the genes encoding human β-glucuronidase variants. All human β-glucuronidase variants being examined had mutations at position 545 (50% T→A and 50% T→S). To determine the effect of amino acid substitutions at position 545 on enzyme activity, the single amino acid mutants T545A (E1-A), T545G (E1-G), T545S (E1-S) and T545Y (E1-Y) were generated and purified from the culture medium of stably transfected fibroblasts. Assay for enzymatic activity at pH 7.0 with the substrate p-nitrophenol 13-D-glucuronide revealed that E1-G and E1-A displayed about 2.5 fold greater activity than wild-type human O-glucuronidase, E1-S exhibited about 1.5 fold greater activity and E1-Y was almost inactive. Thus, the single amino acid substitution at position 545 affected human β-glucuronidase activity at neutral pH.

Independent 3T3 clones ($5 \times 10^7$) in library EP2 mentioned above were immunofluorescence stained with 7G8-FITC and reacted with ELF97 β-D-glucuronide at pH 7.0. Sixteen individual cell clones were isolated after three rounds of sorting and the human β-glucuronidase genes were sequenced. All of the isolated human β-glucuronidase genes possessed identical amino acid substitutions at position 255 (L→Q) and 545 (T→G) with variable substitutions at other positions. Table 1 below lists amino acid substitutions in five exemplary variants and their relative enzymatic activities.

TABLE 1

Amino acid substitutions in selected human β-glucuronidase variants.

| Clone | Amino acid residue positions | | | | | | | Relative activity[a] |
|---|---|---|---|---|---|---|---|---|
| | 159 | 243 | 255 | 518 | 545 | 595 | 599 | |
| Wild type | V | L | L | Q | T | E | T | 1 |
| E1-S | | | | | S | | | 21 |
| E1-G | | | | | G | | | ND[b] |
| S2 | M | | | | S | L | L | 65 |
| S28 | | | | R | S | Y | F | 47 |
| E2-20 | | Q | Q | | G | | | 116 |

[a]Relative activity of membrane-tethered human β-glucuronidase was calculated as the ratio of FL4 (human β-glucuronidase activity)/FL1 (surface human β-glucuronidase expression) at pH 7.0 and normalized to the FL4/FL1 of wild-type human β-glucuronidase. The substrate was ELF97 β-D-glucuronide.
[b]Not determined.

To help differentiate between beneficial and null mutations in the human β-glucuronidase variants, human β-glucuronidase cDNA isolated from the sorted EP1 library (30%) was shuffled with the wild-type human β-glucuronidase gene (70%) to breed out null mutations. The shuffled backcross library, described in section (iii) above, was then expressed on 3T3 fibroblasts and screened with 7G8-FITC and ELF97 β-D-glucuronide at pH 7.0. After one round of flow cytometric sorting, individual cell clones were isolated and the human β-glucuronidase gene was sequenced. Among 13 single-cell clones, amino acid changes at positions 545, 595 and 599 were consistently associated with increased human β-glucuronidase activity at neutral pH values.

The human β-glucuronidase variants identified in this study include amino acid substitutions at positions 159, 243, 255 and 518 on the surface of human β-glucuronidase and positions 545, 595 and 599 near the catalytic pocket. See Islam et al., J. Biol. Chem. 274:23451-23455 (1999). Clone E2-20, which includes 2 mutations on the enzyme surface (L243Q and L255Q), displayed about a three-fold smaller $K_m$ as compared to E1-G which shares a common mutation of T545G. S2 and S28 variants also have mutations in surface amino acids (V159M and Q518R, respectively). Q518 is present on the α6 helix of the TIM barrel. Substitution of glutamine with arginine is unlikely to disrupt the structure of the α-helix, suggesting that the effect of this substitution was mediated by charge effects. In sum, the results obtained from this study show that amino acid substitutions distant from the enzyme's catalytic cavity contributed to enhanced β-glucuronidase activity.

To further examine the influence of varying the amino acids at positions 545, 595 and 599 on the catalytic activity of human β-glucuronidase, the cDNA library generated by saturation mutagenesis, as described in section (iii) above, was screened by two rounds of cell sorting at pH 7.0. Among 14 single-cell clones displaying high activity, seven different amino acids (all non-negatively charged) appeared at position 595. Furthermore, 79% of the human β-glucuronidase variants had serine at position 545 and 13 of 14 clones contained amino acids with hydrophobic side groups (28.5% leucine, 28.5% isoleucine and 43% phenylalanine) at position 599. Two variants, S2 and S28, identified in this screening are listed in Table 1 above.

EXAMPLE 2

Preparation and Characterization of Human Beta-Glucuronidase Variants

Preparation of Human Beta-Glucuronidase Variants

Recombinant His-tagged wild-type human β-glucuronidase and its variants (soluble) were produced in and purified from stable 3T3 fibroblast lines, following the method described above also the method described in Wu et al., Biotechnol Appl Biochem 40:167-172 (2004).

Examination of Enzymatic Activity

The pH-dependent enzyme activities of the above-mentioned recombinant human beta-glucuronidase and variants were measured in triplicate with 0.1 mM ELF97 β-D-glucuronide at 37° C. for 30 minutes at a defined pH ranging from 3-10 in a beta-glucuronidase reaction buffer (50 mM Bis-Tris, 50 mM triethanol amine, 100 mM acetic acid, 0.1% BSA). The reaction was quenched by adding an equal volume of a stop buffer (2 M Tris-HCl, 0.8 M sodium bicarbonate, pH 8). The fluorescence of ELF97 was measured in a Gemini EM microplate spectrofluorometer (Molecular Device, Sunnyvale, Calif.) at excitation/emission wavelengths of 355/555 nm. Kinetic values for human beta-glucuronidase substrate hydrolysis were determined by diluting ELF97 β-D-glucuronide (2 mM) in a pH 4.5 or pH 7.0 beta-glucuronidase reaction buffer 1:1 with defined concentrations of human beta-glucuronidase in 200 μl. Fluorescence was immediately measured under thermal control at 37° C. for 8-10 min. The measurement was repeated using the same amount of enzyme at different substrate concentrations in an optimal range. The acquired readings were converted to product concentration based on preestablished standard curves. Double reciprocal plots were used to determine $K_m$ and $k_{cat}$. Kinetic assays were performed at least 3 times and mean values were calculated. The stability of recombinant human beta-glucuronidase variants was carried out by measuring their enzymatic activity at time 0 and again after incubating 5 μg purified enzymes in PBS (containing 0.5 mg/ml BSA) at 37° C. for 14 days. The enzymatic activities of the human beta-glucuronidase variants were measured in triplicate with 0.5 mM 4-methylumbelliferyl β-D-glucuronide at 37° C. for 15 minutes at pH 7.0 in β-glucuronidase reaction buffer. The reaction was terminated by adding an equal volume of a stop buffer (1 M glycine, 0.5 M sodium bicarbonate, pH 11) and the fluorescence was measured at excitation/emission wavelengths of 355/460 nm in a microplate spectrofluorometer.

The five variants listed in Table 1 above displayed 20 to 115 fold greater enzyme activity than wild-type human β-glucuronidase at pH 7.0. These variants were found to migrated slower than the predicted molecular weight of a human β-glucuronidase monomer due to the presence of N-linked oligosaccharides in the enzyme (see Shipley et al., J Biol Chem 268:12193-12198 (1993). Wild-type human β-glucuronidase displayed maximal activity at pH 4.0 but only 2% of maximal activity at pH 7.0. The variants, on the other hand, exhibited maximal activity at pH 4.5 with relatively broad pH profiles. The kinetic properties of wild-type human β-glucuronidase and its variants were compared at pH 4.5 and pH 7.0, using ELF97 β-D-glucuronide as the substrate. See Table 2 below.

TABLE 2

Kinetic parameters of wild-type human β-glucuronidase and variants thereof at pH 4.5 and 7.0.

| Enzyme | pH 4.5 | | pH 7.0 | |
|---|---|---|---|---|
| | $K_m$ (mM) | $k_{cat}$ (s$^{-1}$) | $K_m$ (mM) | $k_{cat}$ (s$^{-1}$) |
| Wild type | 0.48 ± 0.06 | 175 ± 17 | 2.25 ± 0.67 | 41 ± 6 |
| E1-S | 0.052 ± 0.004 | 117 ± 14 | 0.39 ± 0.04 | 31 ± 6 |
| E1-G | 0.022 ± 0.002 | 106 ± 4 | 0.11 ± 0.01 | 32 ± 4 |
| S2 | 0.0081 ± 0.0008 | 107 ± 7 | 0.035 ± 0.003 | 42 ± 4 |
| S28 | 0.016 ± 0.003 | 79 ± 3 | 0.072 ± 0.024 | 26 ± 3 |
| E2-20 | 0.0067 ± 0.0005 | 71 ± 3 | 0.038 ± 0.005 | 30 ± 5 |

The values listed in Table 2 are mean values of triplicate determinations ± SD.

Figure 2A:
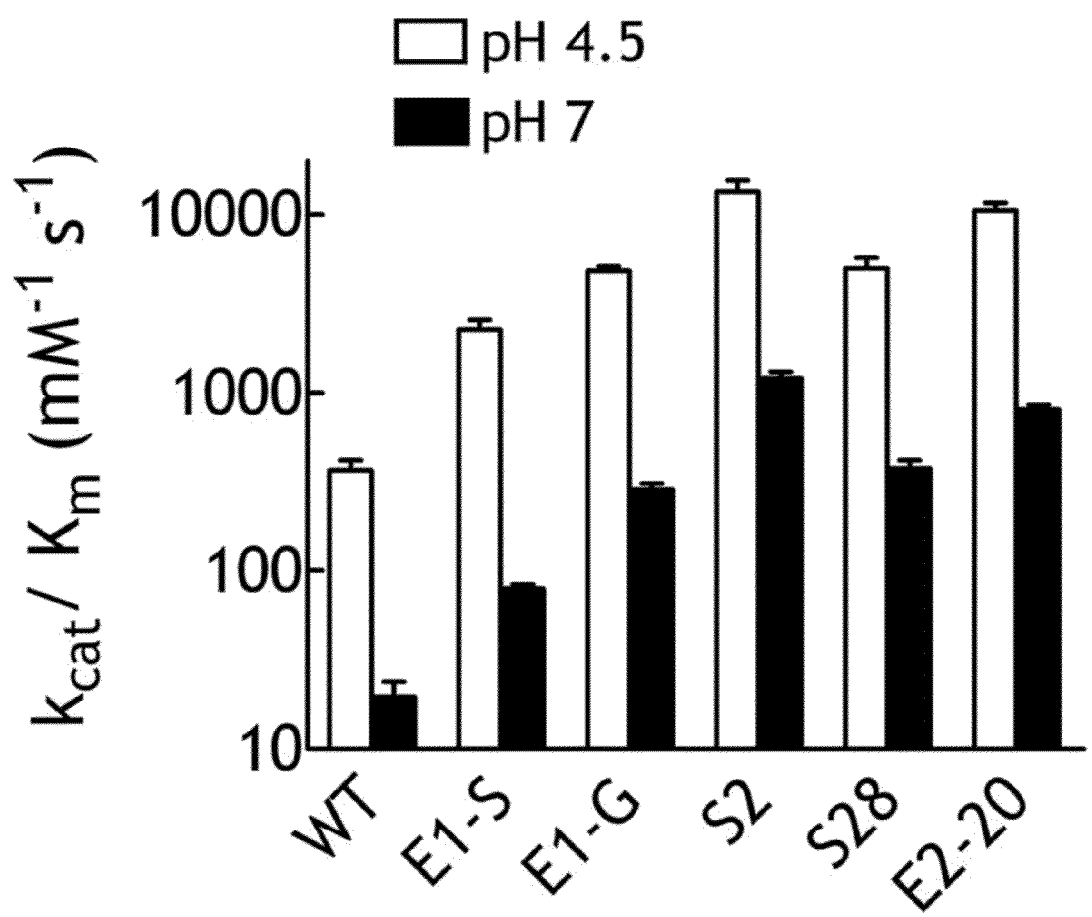
FIG. 2A is a chart showing enzymatic activity of wild-type human beta-glucuronidase and variants E1-S, E1-G, S2, S28, and E2-20 at pH 4.5 or 7.
Figure 2B:
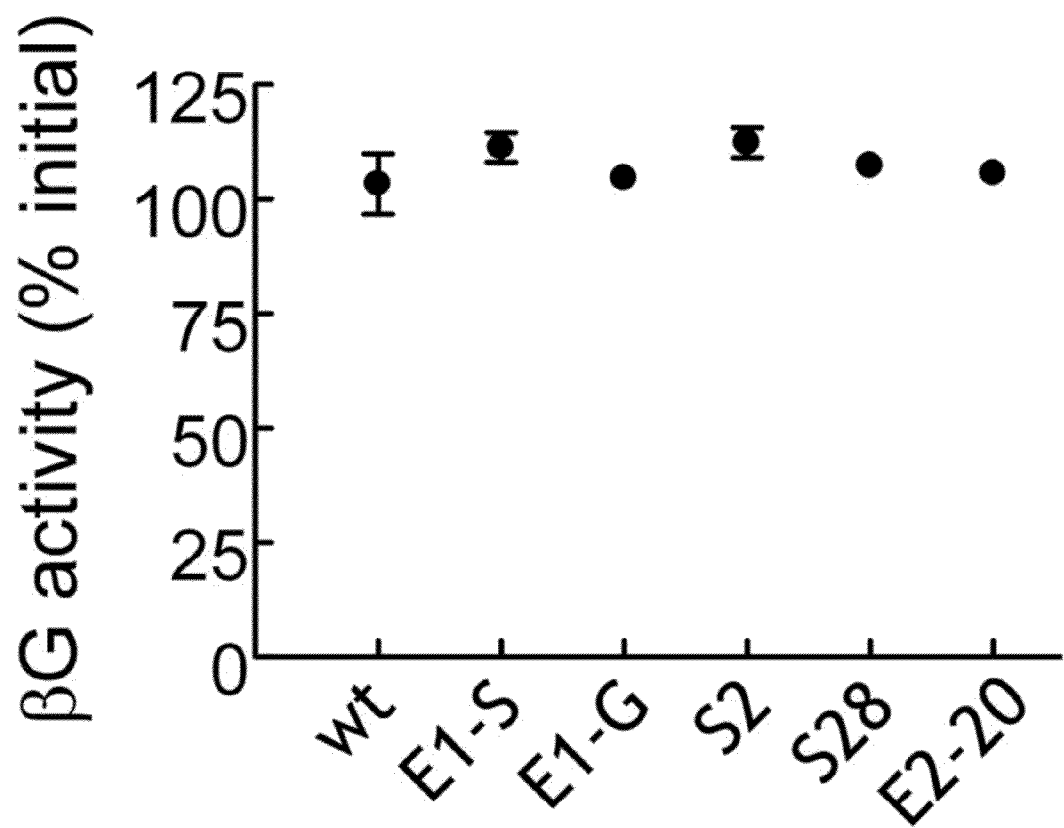
FIG. 2B is a diagram showing enzymatic activity of wild-type human beta-glucuronidase and variants E1-S, E1-G, S2, S28, and E2-20 after incubation for 14 days at 37° C., pH 7.0.

Consistent with enhanced enzymatic activity of membrane-bound human beta-glucuronidase variants, the soluble human beta-glucuronidase variants displayed enhanced $k_{cat}/K_m$ values at both pH 4.5 and 7.0. See FIG. 2A. At pH 7.0, E1-S and E1-G displayed $k_{cat}/K_m$ values 4-fold and 10-fold higher than wild-type human β-glucuronidase whereas S2, S28 and E2-20 variants displayed 20-fold to 60-fold enhancements in $k_{cat}/K_m$. Surprisingly, the $k_{cat}/K_m$ values of the S2 and E2-20 enzymes at pH 7.0 were about 2-fold greater than the $k_{cat}/K_m$ of the wild-type human beta-glucuronidase at pH 4.5. The dramatic increases in substrate affinity at acidic and neutral pH explain the overall enhancement in the activities of the human beta-glucuronidase variants. The enzymatic activity of the recombinant human β-glucuronidase variants at pH 7.0 was fully retained for at least two weeks at 37° C., indicating that the mutant enzymes displayed good stability under physiological conditions. See FIG. 2B.

Prodrug Activation by Human β-glucuronidase Variants

Figure 3A:
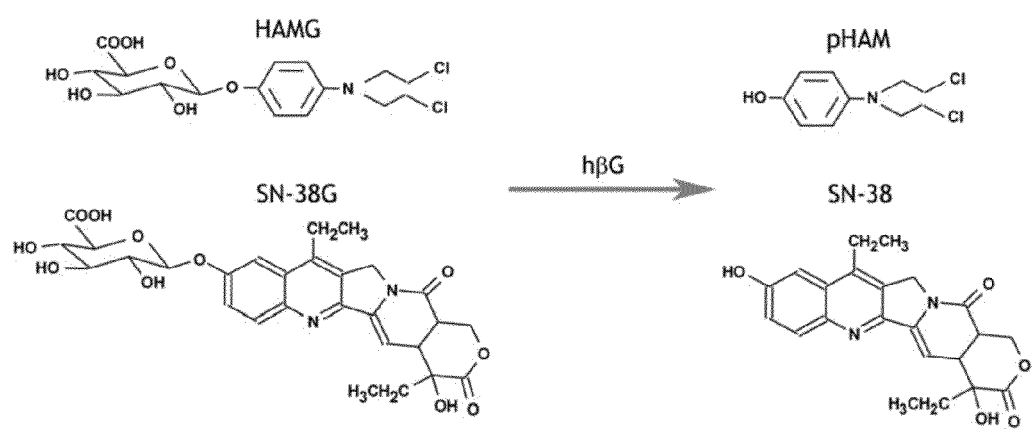
FIG. 3A is a diagram showing that human beta-glucuronidase converts prodrugs HAMG and SN-38G to active drugs pHAM and SN-38, respectively.
Figure 3B:
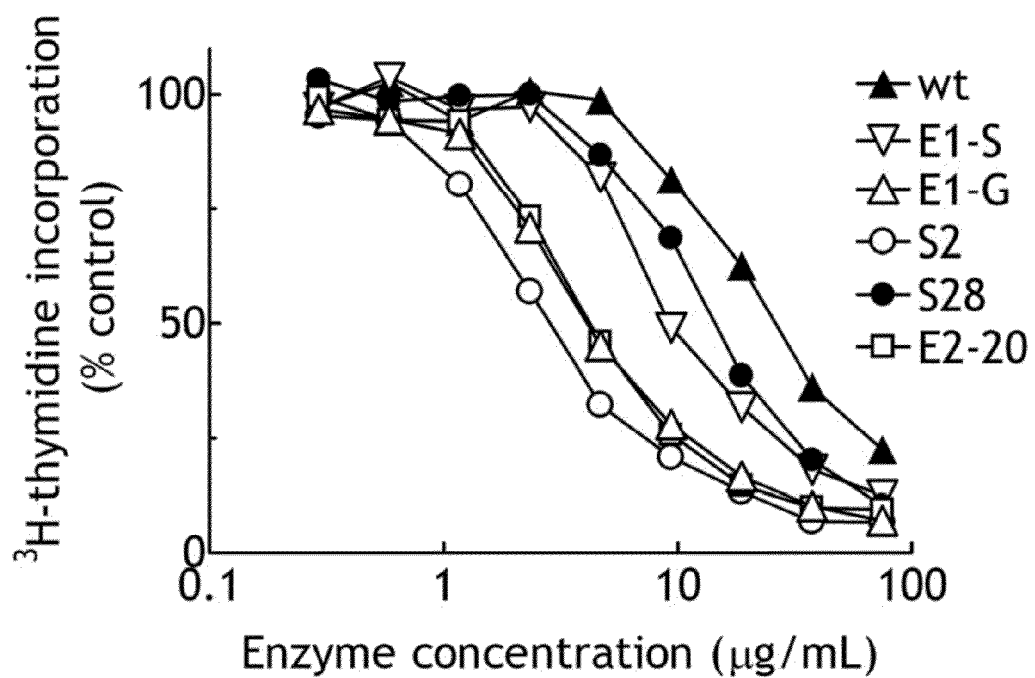
FIG. 3B is a chart showing inhibition of tumor cell proliferation by prodrug HAMG and wild-type human beta-glucuronidase or one of variants E1-S, E1-G, S2, S28, and E2-20 at various enzyme concentrations. Tumor cell proliferation is indicated by $^3$H-thymidine incorporation into DNAs.
Figure 3C:
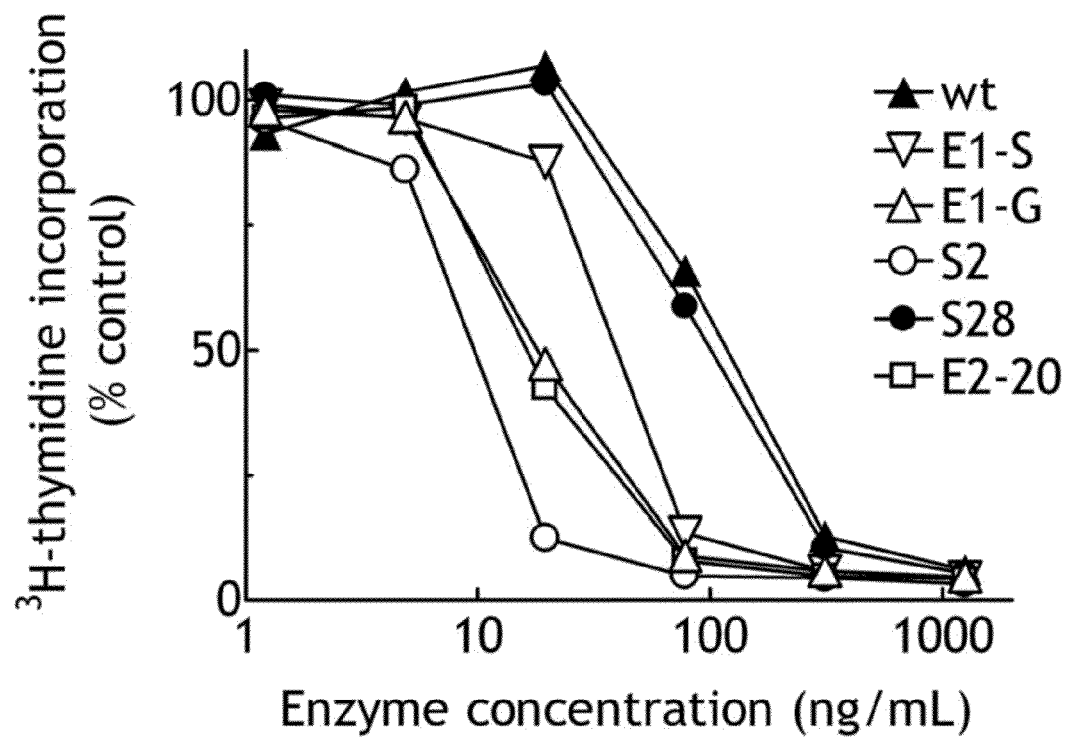
FIG. 3C is a chart showing inhibition of tumor cell proliferation by prodrug SN-38G and wild-type human beta-glucuronidase or one of variants E1-S, E1-G, S2, S28, and E2-20 at various enzyme concentrations. Tumor cell proliferation is indicated by $^3$H-thymidine incorporation into DNAs.

The prodrug activation activity of the human beta-glucuronidase variants was determined as follows. EJ human bladder cancer cells were incubated with graded concentrations (see FIGS. 3B and 3C) of human β-glucuronidase variants in RPMI (pH 6.8) containing either 10 μM HAMG or 100 nM SN-38G for 24 hours. The cells were further incubated for 24 hours in fresh medium before incorporation of $^3$H-thymidine into cellular DNA was measured following the procedure described below. HAMG is a non-toxic glucuronide prodrug of p-hydroxyaniline mustard (pHAM), which is cytotoxic and SN-38G is the inactive form of SN-38, an anti-cancer drug. See FIG. 3A.

Purified recombinant human beta-glucuronidase and its variants with defined concentrations were mixed with 10 μM HAMG or 100 nM SN-38G and the mixture was added to 5000 EJ human bladder cancer cells in 200 μl complete medium at pH 6.8 for 24 h. The cells were washed and incubated in fresh medium for 24 h and then pulsed for 16 h with $^3$H-thymidine (1 μCi/well). The cells were harvested and the radioactivity was measured in a TopCount Microplate Scintillation Counter (Packard, Meriden, Conn.). Results are expressed as percent inhibition of $^3$H-thymidine incorporation into cellular DNA in comparison to untreated cells.

All human β-glucuronidase variants hydrolyzed HAMG to pHAM more efficiently than the wild-type human β-glucuronidase as demonstrated by enhanced killing of EJ cancer cells. Form example, the S2 variant was 9-fold more effective than the wild-type human beta-glucuronidase ($EC_{50}$=2.7 vs. 24 μg/mL, respectively). A similar result was found for SN-38G, which releases the potent topoisomerase I poison SN38 (see Rivory, Clinical and experimental pharmacology & physiology 23:1000-1004 (1996) upon hydrolysis of the glucuronide moiety. See FIGS. 3B and 3C. The $EC_{50}$ of the wild-type human beta-glucuronidase and the S2 variant were 96 and 8.4 ng/ml, respectively, representing an 11-fold improvement in prodrug activation. The above results demonstrate that the human beta-glucuronidase variants tested in this study more effectively hydrolyzed two structurally distinct anti-cancer glucuronide prodrugs at neutral pH.

EXAMPLE 3

Figure 4A:
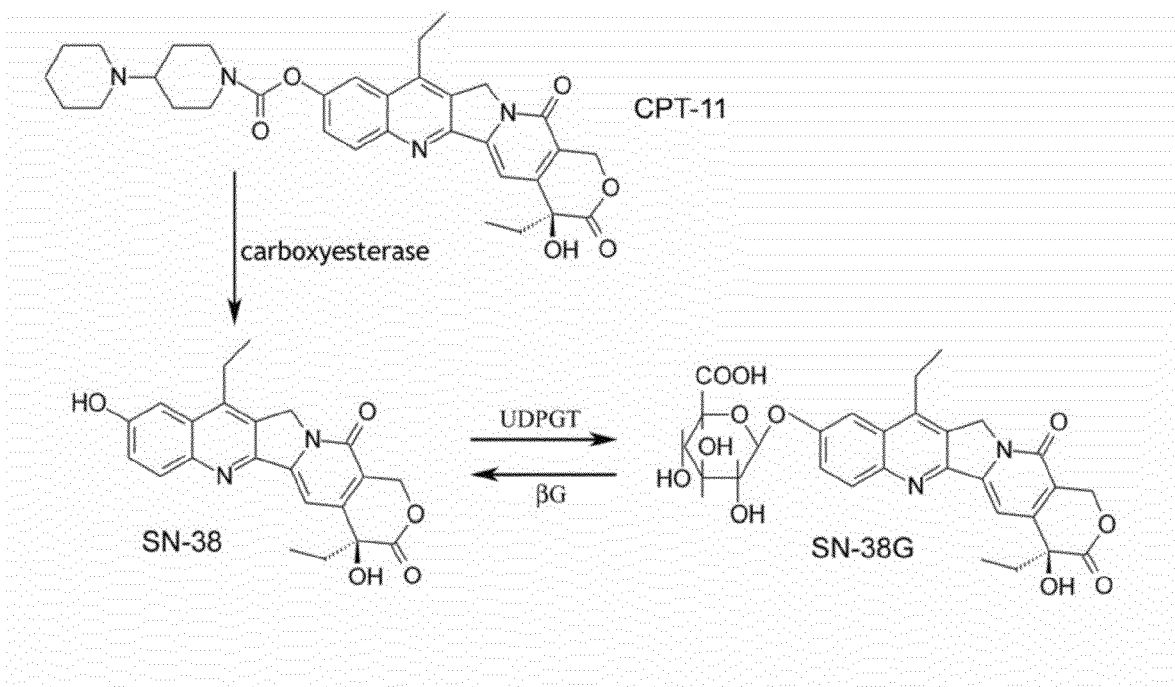
FIG. 4A is a diagram showing metabolism of CPT-11.
Figure 4B:
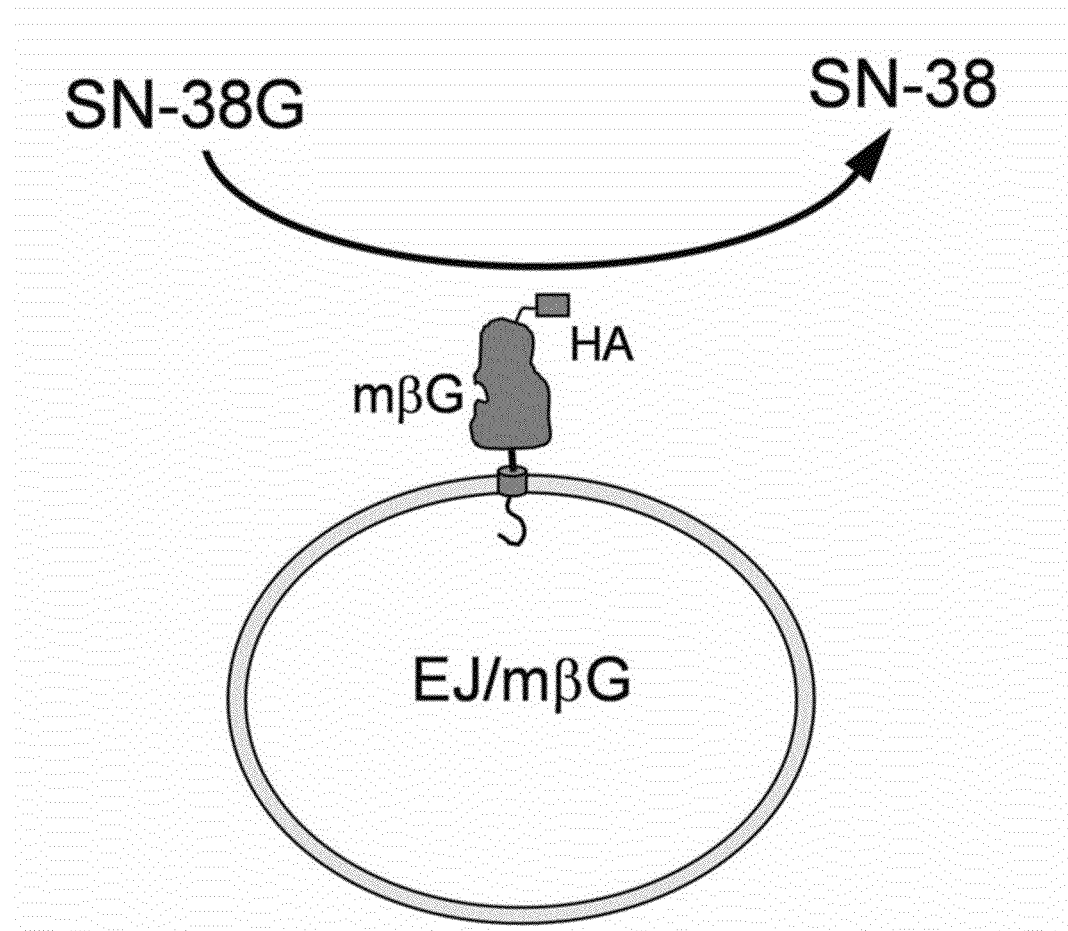
FIG. 4B is a diagram showing surface expression of mouse beta-glucuronidase on cancer cells and conversion of prodrug SN-38G to active drug SN-38 by the glucuronidase on cancer cells. An HA tag is linked to the N-terminus of the glucuronidase.

Enhancing CPT-11 Anti-Tumor Activity with Beta-Glucuronidase Expressed on Tumor Cells In vitro Assay EJ human bladder carcinoma cells were cultured in RPMI medium supplemented with 10% bovine calf serum in a humidified atmosphere of 5% $CO_2$ in air at 37° C. The cells were engineered to express membrane-localized mouse beta-glucuronidase by attaching a linker, a transmembrane domain, and a cytoplasmic tail to the c-terminus of the enzyme (see FIG. 4A), as described in Chen et al., 2007. An HA tag is present at the N-terminus of mouse beta-glucuronidase. See FIG. 4B. Permanent EJ cells expressing membrane-localized mouse beta-glucuronidase (EJ/mβG) were generated by retroviral transduction of EJ cells, following the method described in Example 1 above.

The EJ or EJ/mβG cells ($5 \times 10^5$) were stained 45 min with 0.1 μg rat anti-HA mAb in 50 μl RPMI medium or with 5 μg mAb 7G7 in 500 μl RPMI. The cells were washed with RPMI three times and incubated 45 min with 1.5 μg goat anti-rat-FITC in 200 μl RPMI. After the cells were washed three times with medium, 5 μg/ml propidium iodide was added to them. The fluorescence (excitation 488 nm, emission 530 nm) of 10,000 viable cells was measured on a FACSAdvantage SE (BD Biosciences, Mountain View, Calif.). The results confirm localization of the beta-glucuronidase on the surface of EJ/mβG cells.

Figure 5:
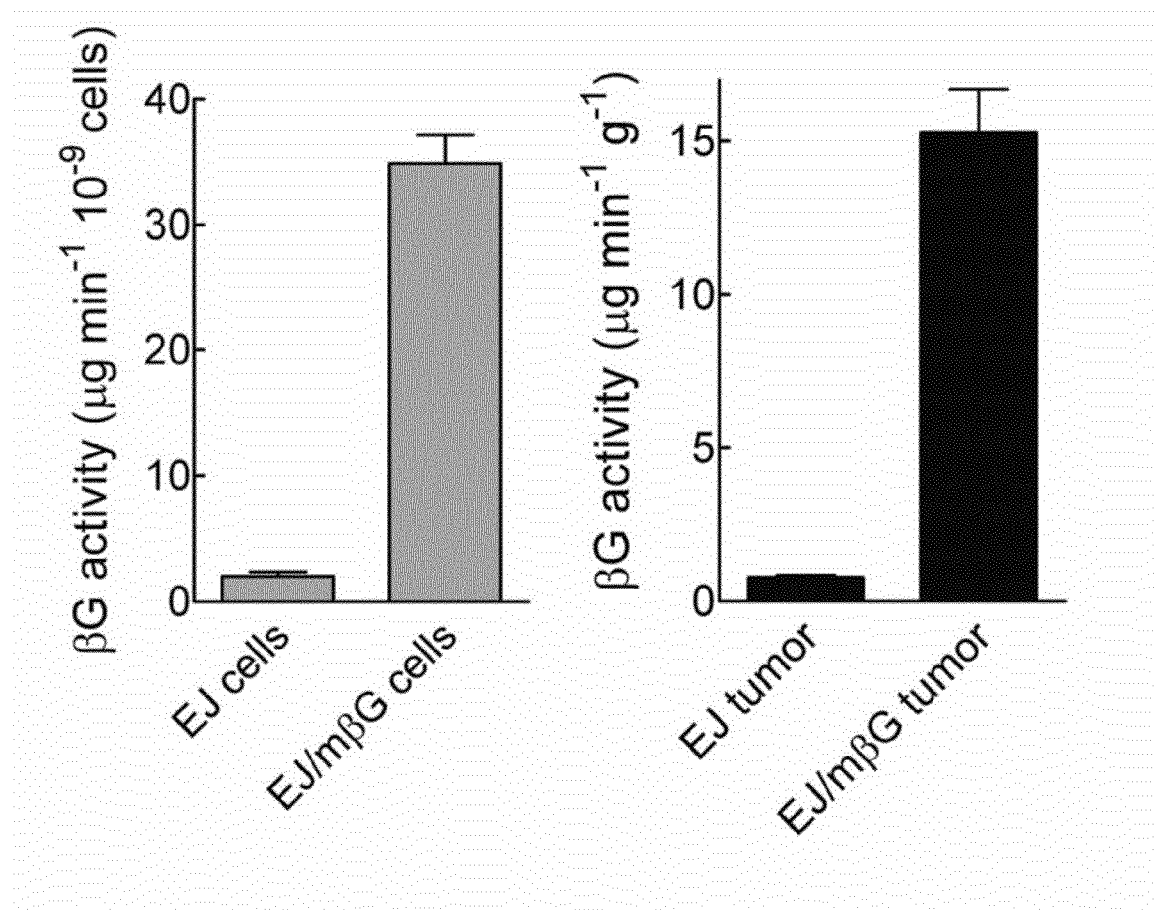
FIG. 5 is a chart showing beta-glucuronidase activity in EJ human bladder cancer cells (EJ) and EJ cells expressing mouse beta-glucuronidase (EJ/mβG), as well as in tumor homogenates from EJ and EJ/mβG xenografts.

EJ and EJ/mβG cells grew with similar rates and doubling times of ~24 h. Using p-nitrophenol β-D-glucuronide as a substrate, the beta-glucuronidase activity in both EJ and EJ/mβG cells were examined following the method described in Cheng et al., Cancer Gene ther. 15:393-401 (2008). The results indicate that cultured EJ/mβG cells and displayed significantly more enzymatic activity than EJ cells, verifying that the membrane-bound beta-glucuronidase was functional. See FIG. 5.

The sensitivity of EJ and EJ/mβG cells to CPT-11, SN-38, and SN-38G was investigated at neutral pH (7.4) or at a slightly acidic pH (6.6) as follows. CPT-11 was obtained from Sigma-Aldrich (St. Loius, Mo.), SN-38 was from ScinoPharm (Shan-Hua, Taiwan), and SN-38G was isolated and HPLC-purified from the urine of mice treated with CPT-11.

Figure 6A:
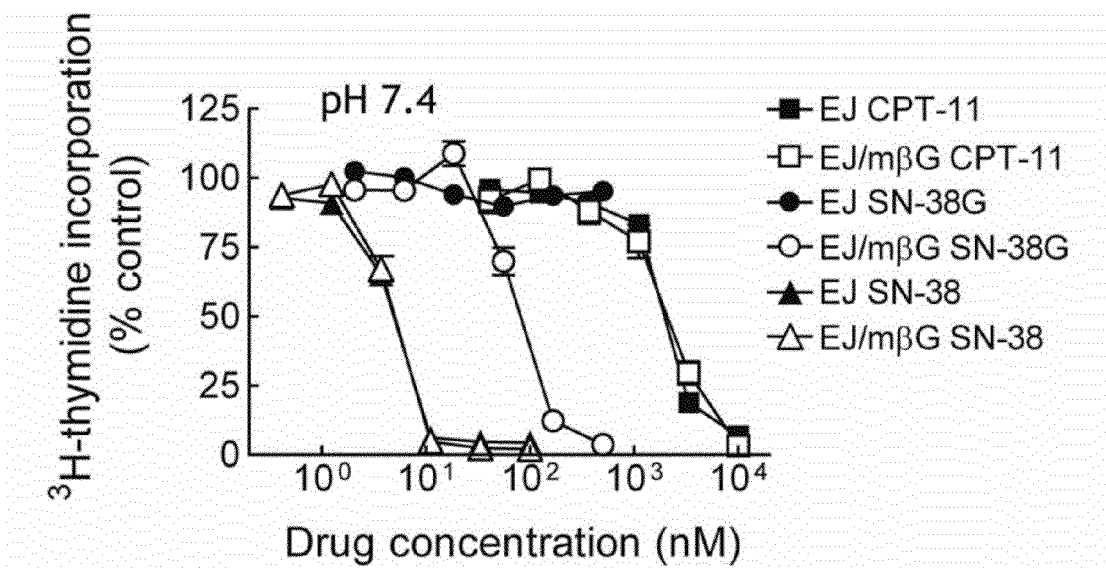
FIG. 6A is a chart showing inhibition of EJ or EJ/mβG cell proliferation by SN-38G or CPT-11 under various concentrations at pH 7.4. Tumor cell proliferation is indicated by $^3$H-thymidine incorporation into DNAs.

The cells were exposed for 24 h at pH 7.4 or pH 6.6 to graded concentrations of CPT-11, SN-38 or SN-38G. See FIG. 6A. pH 6.6 was examined to investigate the effect of slightly acidic pH, as found in some tumors (Murdter et al., J Pharmacol Exp Ther 301:223-228, 2002), on drug cytotoxicity. Cell viability was examined by measuring $^3$H-thymidine incorporation into cellular DNA after the cells were cultured for an additional 24 h in fresh medium. More specifically, the pH of EJ or EJ/mβG cell medium was adjusted to pH 6.6 or 7.4 by addition of HCl or NaOH immediately before adding graded concentrations of drugs prepared from stock solutions of 1 mg/ml CPT-11, 1 mg/ml SN-38 or 0.1 mg/ml SN-38G in DMSO and $^3$H-thymidine (1 μC/well) was measured as described in Cheng et al., 2008.

Figure 6B:
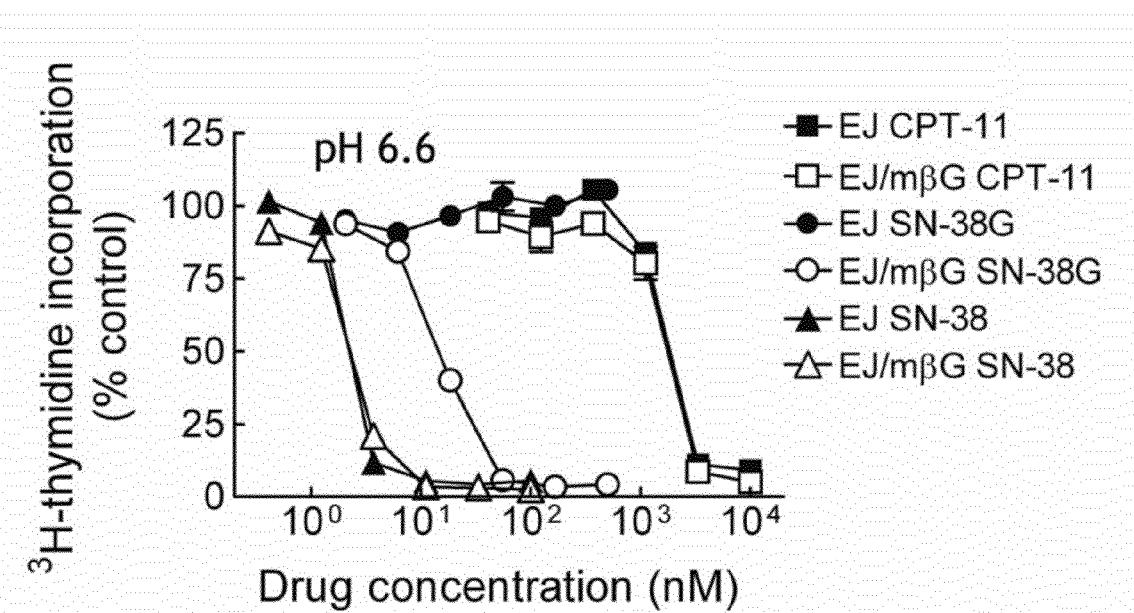
FIG. 6B is a chart showing inhibition of EJ or EJ/mβG cell proliferation by SN-38G or CPT-11 under various concentrations at pH 6.6. Tumor cell proliferation is indicated by $^3$H-thymidine incorporation into DNAs.

Both the cell lines were equally sensitive to CPT-11 or SN-38 in vitro. CPT-11 displayed relatively low cytotoxicity to both EJ and EJ/mβG cells with $IC_{50}$ values of ~2100 nM. This prodrug was 400 to 800 times less toxic than SN-38 to both EJ and EJ/mβG cells. SN-38, by contrast, exhibited potent cytotoxicity against EJ and EJ/mβG cells with $IC_{50}$ values of 6 nM at pH 7.4 (see FIG. 6A) and 2 nM at pH 6.6 (see FIG. 6B). The similar sensitivities of EJ and EJ/mβG cells to CPT-11 and SN-38 along with their similar in vitro growth rates indicates that surface expression of beta-glucuronidase did not alter the basic properties of EJ cancer cells.

SN-38G was non-toxic to EJ cells in vitro at the highest concentration investigated (i.e., 1000 nM). On the other hand, EJ/mβG cells were more sensitive to SN-38G (over 30 times), suggesting that the membrane-bound beta-glucuronidase hydrolyzed SN-38G to cytotoxic SN-38, resulting in dramatically enhanced cytotoxicity of SN-38G to EJ/mβG cells with an $IC_{50}$ value of 190 nM at p 7.4 and 32 nM at pH 6.6.

In Vivo Assay

Three to four month old Beige-SCID female mice were used in this study. The mice were maintained under SPF conditions and were fed a standard laboratory diet with free access to food and water, under artificial circadian rhythm. EJ or EJ/mβG cells were injected into the mice subcutaneously in their right flank to form tumor xenografts. Both types of cancer cells displayed similar in vivo growth rates, indicating that surface expression of the beta-glucuronidase did not affect cell properties.

Unfixed tumor sections were stained with H&E or incubated for 10 min with 1 mg/ml 5-bromo-4-chloro-3-indolyl β-D-glucuronide in 0.1 M acetate buffer, pH 4.6 containing 5 mM $K_3Fe(CN)_6$ and 5 mM $K_2Fe(CN)_6$. The slides were washed twice with PBS and counterstained for 5 min with Nuclear Fast Red. Slides mounted in GVA mount (Zymed) were examined under an optical microscope (Olympus). Sections from EJ and EJ/mβG xenografts displayed similar morphologies, suggesting that drug penetration into these tumors similarly.

Tumor samples were immediately dispersed in ice-cold acidic methanol (methanol: water: perchloric acid=20:20:1) and homogenized 60 sec on an Ultraturax tissue homogenizer at 20,000 rpm to produce tumor homogenates. These homogenates were assayed for beta-glucuronidase activity as described in Cheng et al., 2008. The result indicates that tumor homogenates from mice bearing EJ/mbG xenografts displayed significantly more enzymatic activity than tumor homogenates from mice bearing EJ xenografts, confirming that the surface-expressed beta-glucuronidase was functionally active. See FIG. 5. Beta-glucuronidase activity was also clearly evident on EJ/mβG tumor sections but not EJ tumor sections as detected by enzyme histochemical staining, confirming that the beta-glucuronidase was retained and active on tumors in vivo.

Groups of Beige-SCID mice bearing 150-250 mm$^3$ (calculated by 0.5×length×width×height) EJ or EJ/mβG subcutaneous xenografts were i.v. injected on two consecutive days with 10 mg/kg CPT-11 or PBS. The tumor sizes and body weights were examined for 2 weeks.

The intratumoral distribution of CPT-11 was examined as follows. Tumors were collected 2, 8 and 24 h after CPT treatment, immediately dispersed in ice-cold acidic methanol (methanol: water: perchloric acid=20:20:1), and homogenized 60 sec on an Ultraturax tissue homogenizer at 20,000 rpm. The samples were clarified by centrifugation at 15,000 g for 5 min at 4° C. Supernatants were diluted with 0.1 M $KH_2PO_4$ and then separated by SPE-HPLC on a μBondapack column with 27% acetonitrile in 0.1 M potassium phosphate buffer pH=2.6. The analytes were detected on a JASCO 2020 fluorescence detector (Jasco, Japan) (at 375 nm excitation and 430 nm emission for SN-38G and CPT-11 and at 540 nm emission for SN-38). These three analytes were quantified by comparison with standard curves generated with analyte concentrations ranging from 2.0 pg to 200 ng. The results from this study show that the intratumoral CPT-11 concentrations were identical in both EJ and EJ/mβG tumors, indicating that CPT-11 distributed in these two types of tumors in the same manner. On the other hand, SN-38 concentrations were 65-130% higher and SN-38G concentrations were 40-50% lower in EJ/mβG tumors as compared to EJ tumors (see Table 3 below), demonstrating that specific hydrolysis of SN-38G to SN-38 took place in tumors expressing extracellular beta-glucuronidase.

TABLE 3

CPT-11, SN-38 and SN-38G concentrations in EJ and EJ/mβG xenografts

| (Pro)drug | Time (h) | EJ (ng drug/g tumor) | EJ/mβG (ng drug/g tumor) | Difference (%) |
|---|---|---|---|---|
| CPT-11 | 2 | 1350 ± 200 | 1500 ± 230 | 14.95 |
|  | 8 | 87 ± 17 | 77 ± 178 | −10.92 |
|  | 24 | 0.58 ± 0.09 | 0.63 ± 0.11 | −8.6 |
| SN-38 | 2 | 43 ± 10.5 | 71 ± 13 | 65.63* |
|  | 8 | 7.5 ± 0.93 | 17 ± 5.56 | 127.10* |
|  | 24 | 0.07 ± 0.02 | 0.12 ± 0.01 | 71.43* |
| SN-38G | 2 | 110 ± 21 | 62 ± 17 | −43.92* |
|  | 8 | 21 ± 5.0 | 13 ± 1.6 | −38.97* |
|  | 24 | 0.32 ± 0.05 | 0.17 ± 0.01 | −46.87* |

The values listed in Table 3 are mean values ±SD of four measurements. Differences are calculated taking EJ values as 100%. Asterisks indicate statistically significant difference of $P<0.05$. Differences in mean values (in all studies discussed herein) were analyzed by the independent student's t-test for unequal variances. P values of less than 0.05 were considered statistically significant.

Figure 7A:
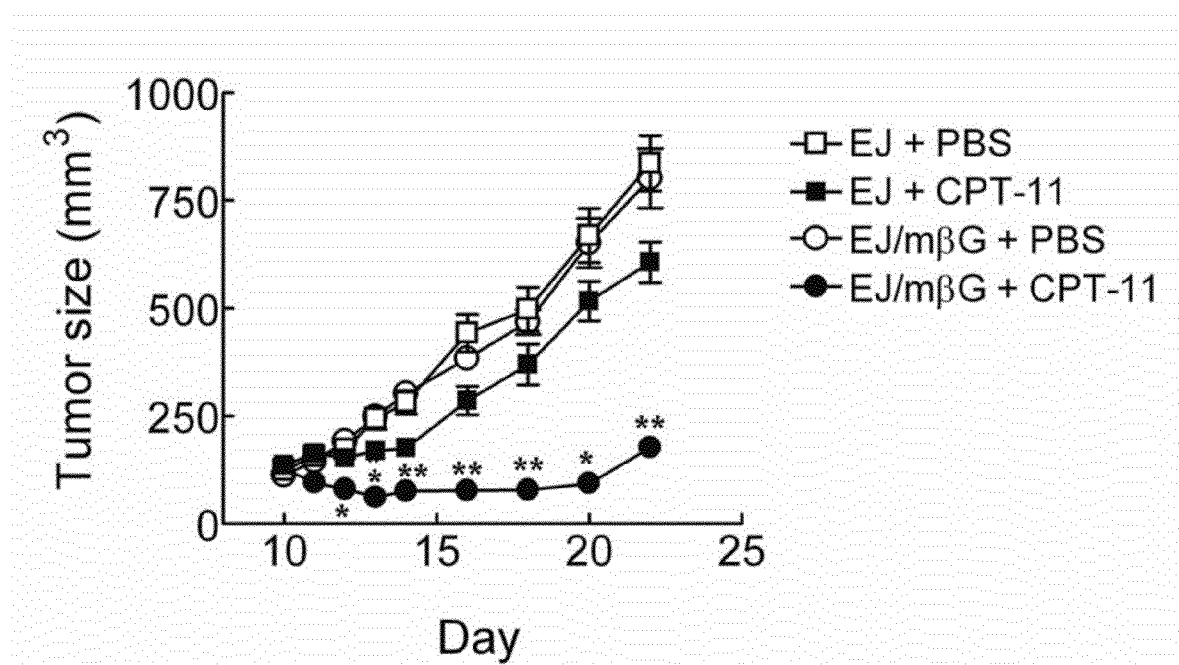
FIG. 7A is a chart showing inhibition of tumor growth by CPT-11 in the presence or absence of moust beta-glucuronidase.
Figure 7B:
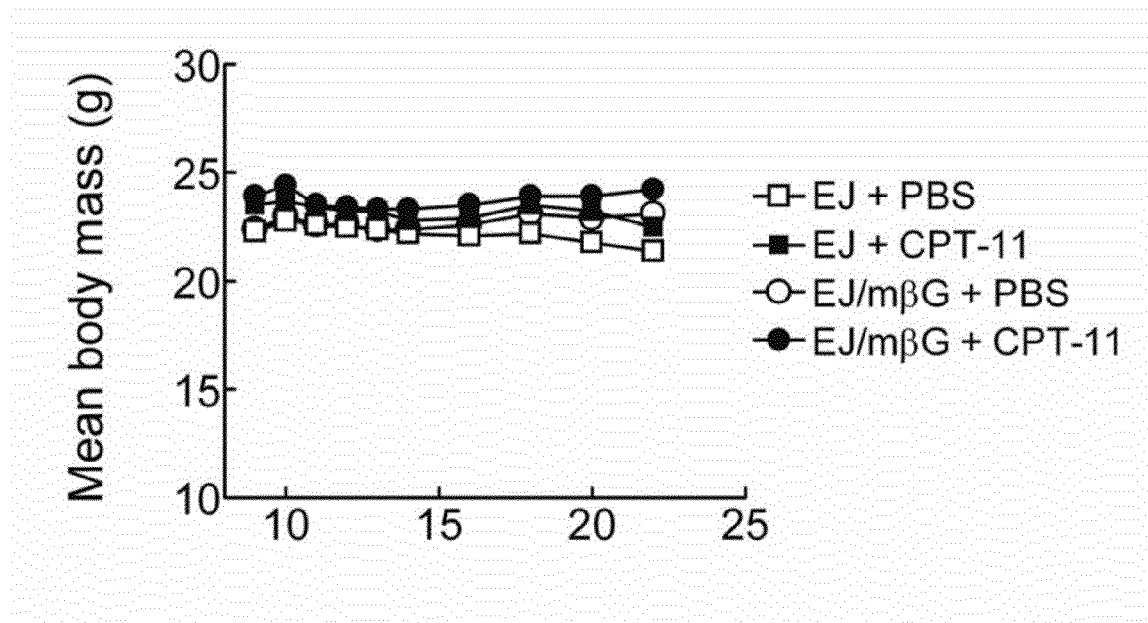
FIG. 7B is a chart showing mean body mass in CPT-treated mice bearing EJ or EJ/mβG xenografts.
Figure 7C:
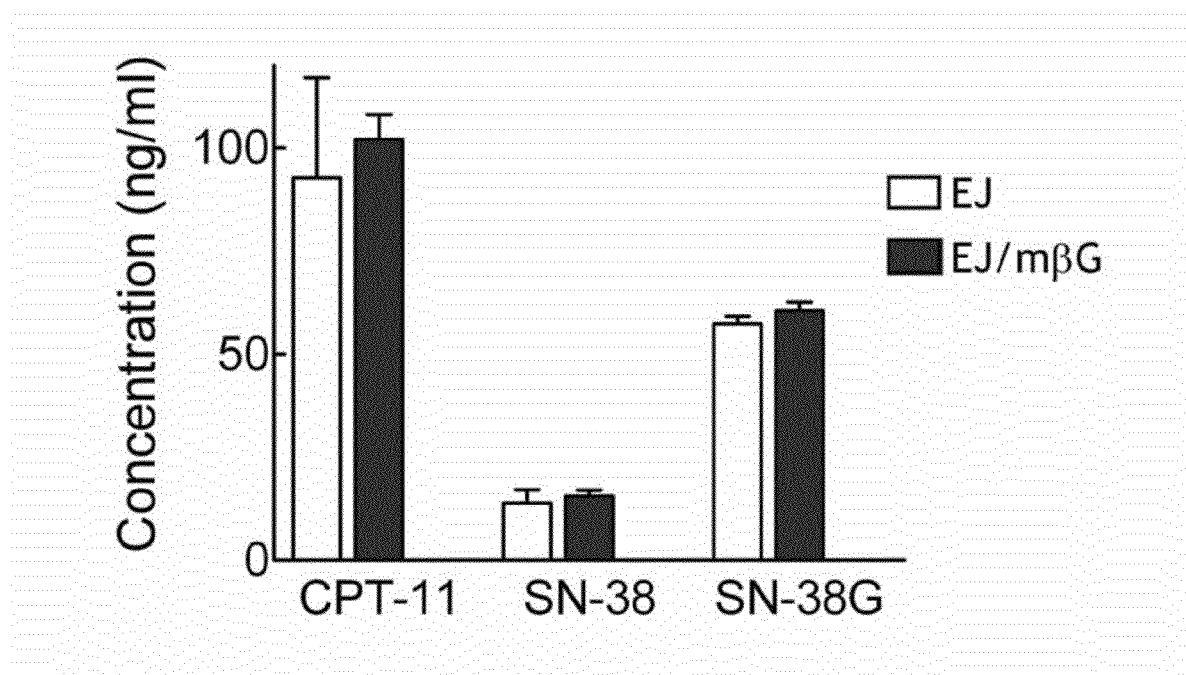
FIG. 7C is a chart showing serum concentrations of CPT-11, SN-38, and SN-38G in mice bearing EJ or EJ/mβG xenografts.

The sizes of the tumor xenografts were measured to examine the anti-tumor effect of CPT-11. As shown in FIG. 7A, CPT-11 did not significantly delay EJ tumor growth at the dose of 10 mg/g, while this prodrug significantly delayed the growth of EJ/mβG tumors, indicating that CPT-11 produced remarkably greater anti-tumor activity against EJ/mβG tumors as compared to EJ tumors. Importantly, CPT-11 treatment-associated toxicity, as judged by body weight, did not increase in mice bearing EJ/mβG tumors. See FIG. 7B.

CPT-11, SN-38 and SN-38G levels in the serum of mice bearing EJ and EJ/mβG tumor were similar at 2 h after CPT-11 administration. See FIG. 11C. Likewise, no significant differences in CPT-11, SN-38 or SN-38G concentrations in those mice were observed at 8 h or 24 h after CPT-11 administration. These results indicate that tumor-located beta-glucuronidase did not affect systemic drug distribution or produce increased levels of SN-38 in the circulation. Thus, preferential intratumoral generation of SN-38 by tumor-located beta-glucuronidase significantly increased the anti-tumor activity of CPT-11 without producing additional systemic toxicity.

In conclusion, the data shown above demonstrates that tumor-localized membrane-bound beta-glucuronidase significantly improved the therapeutic outcome of CPT-11 treatment by converting the large amounts of inactive CPT-11 metabolite (SN-38G) to a potent anti-cancer agent (SN-38), thereby enhancing the anti-tumor efficacy of CPT-11.

EXAMPLE 4

Preparation of Beta-Glucuronidase-Antibody Fusion Proteins

A single-chain humanized antibody (hCC49) against the TAG-72 antigen, as described in Yoon et al., J Biol Chem 281:6985-6992 (2006), was generated by synthetic oligonucleotides, which were designed according to Yoon et al., 2006. The resulting 800 by fragment was subcloned to the pLHCX retroviral vector as described in Wu et al., Biotechnol Appl Biochem 40:167-172 (2004), after restriction enzymes cutting by SfiI and XbaI. The wild-type hβG gene was fused to the 3' end of the humanized CC49 scFv gene to create a fusion gene encoding the hCC49 scFv-hβG (hCC49-hβG) fusion protein. This pLHCX vector includes an immunoglobulin Vκ signal peptide to allow secretion of the fusion protein, an HA tag for detection, and a C-terminal polyhistidine tag for purification.

The gene (SEQ ID NO:3) coding the active human βG mutant (S2) was fused to the CC49 scFv gene for expression of a hCC49—S2 fusion protein, following the same method described above. An anti-dansyl scFv was generated as a control with primers: DNS-F5'-ctggggcccagccggccagt-gaagtg-3') (SEQ ID NO: 20), and DNS-R(5'-ATATCTA-GATCCGCCGCCACCCGACCC ACCACCTCCTGAAC-CGCCTCCACGTTT-3'), (SEQ ID NO: 21), utilizing pLNCX-DNS-B7 (see Cheng, T. L. et al., Cancer Gene Ther 11: 380-388; 2004) as a template. This control scFv was fused to the S2 hβG gene for expressing the control αDNS-S2 fusion protein.

The fusion genes mentioned above, inserted into pLHCX, a retroviral expression vector, were first introduced into GP293 together with the pVSV-G plasmid (Clontech, Mountainview, Calif.) to produce recombinant retroviral particles. 3T3 fibroblast cells were infected with the retroviral particles and cell lines stably expressing the encoded fusion proteins were constructed via routine technology. Recombinant His-tagged fusion proteins were expressed in large scale cultures (Celline 1000 culture flasks) and purified by nickel-chelate chromatography as previously described in Wu et al., 2004. As determined by SDS-PAGE, the recombinant enzyme-antibody fusion proteins thus obtained were substantially pure.

Figure 8:
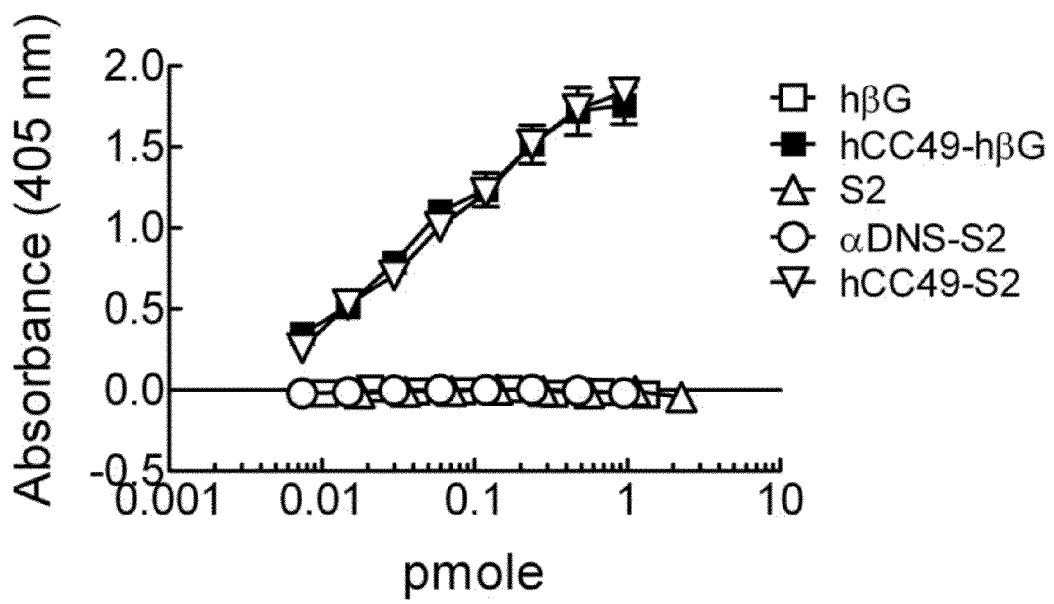
FIG. 8 is a chart showing specific binding of fusion polypeptides hCC49-S2 and hCC49-hβG to mucin.

The antigen-binding activity of the enzyme-antibody fusion proteins mentioned above was measured by ELISA in 96-well microtiter plates coated with bovine submaxillary gland mucin. See King, D. J. et al., Cancer Research 54:6176-6185 (1994). As shown in FIG. 8, hCC49-S2 and hCC49-hβG fusion proteins preserved antigen-binding activity while the αDNS-S2 control did not bind to the mucin antigen.

Figure 9:
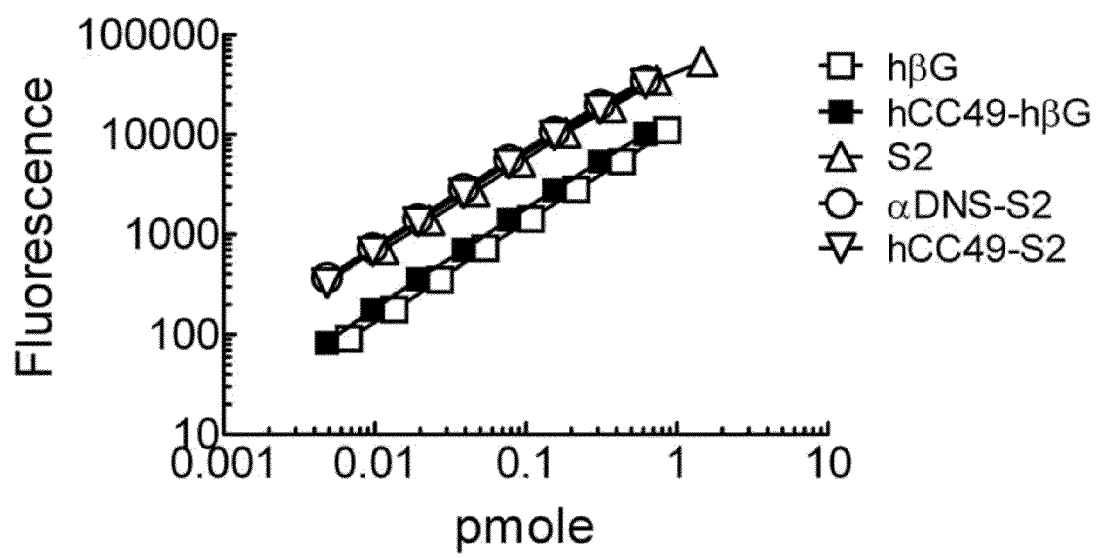
FIG. 9 is a chart showing enzymatic activity of fusion polypeptides hCC49-S2 and hCC49-hβG.

Next, the beta-glucuronidase activity of the fusion proteins was measured by adding 0.5 mM 4-methylumbelliferyl β-D-glucuronide in a beta-glucuronidase reaction buffer (50 mM Bis-Tris, 50 mM triethanol amine, 100 mM acetic acid, 100 ng/ml bovine serum albumin, pH 7.0) for 30 minutes at 37° C. The reaction was terminated by adding an equal volume of stop buffer (1 M glycine, 0.5 M sodium bicarbonate, pH 11). The fluorescence of 4-MU was measured at excitation/emission wavelengths of 355/460 nm in a Gemini EM microplate spectrofluorometer (Molecular Device, Sunnyvale, Calif.). The results indicate that hCC49-hβG fusion protein displayed similar βG activity as wild-type hβG. See FIG. 9. Fusion proteins hCC49—S2 and αDNS-S2 displayed similar βG activity as the S2 hβG variant. In addition, hCC49-S2, αDNS-S2 and S2 exhibited significantly greater enzymatic activity than the wild-type hβG. See also FIG. 9.

Taken together, the above data clearly demonstrate that the hCC49-hβG and hCC49-S2 fusion proteins retained both the antigen-binding activity of their antibody moiety and the enzymatic activity of their glucuronidase moiety.

Other Embodiments

All of the features disclosed in this specification may be combined in any combination.

Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A polypeptide comprising an amino acid sequence, wherein the amino acid sequence is selected from the group consisting of SEQ ID NOs:6-10.

2. The polypeptide of claim 1, further comprising the amino acid sequence of a single-chain antibody that specifically targets cancer cells.

3. The polypeptide of claim 2, wherein the single-chain antibody is CC49 scFv.

4. The isolated polypeptide of claim 2, wherein the single-chain antibody is a human or humanized antibody.

5. The polypeptide of claim 1, further comprising the amino acid sequence of a peptide that particularly targets cancer cells.

6. The polypeptide of claim 5, wherein the peptide is selected from the group consisting of AHNP, RGD4C, HN-1, CSNRDARRC (SEQ ID NO: 12), CNGRCVSGCAGRC (SEQ ID NO: 13), $Z_{HER2:342-pep2}$, ZEGFR:1907, and SP94.

7. A glucuronidase conjugate, comprising a human beta-glucuronidase mutant associated with a cancer-targeting agent, wherein the beta-glucuronidase mutant has the amino acid sequence of one of SEQ ID NOs:6-10.

8. The glucuronidase conjugate of claim 7, wherein the cancer-targeting agent is an antibody specifically binding to cancer cells.

9. The glucuronidase conjugate of claim 8, wherein the antibody is a human or humanized antibody.

10. The glucuronidase conjugate of claim 7, wherein the cancer-targeting agent is a peptide specifically binding to cancer cells.

11. The glucuronidase conjugate of claim 7, wherein the cancer-targeting agent is an aptamer.

* * * * *

SEQUENCE LISTING

```
<160> NUMBER OF SEQ ID NOS: 21

<210> SEQ ID NO 1
<211> LENGTH: 1911
<212> TYPE: DNA
<213> ORGANISM: Artificial Sequence
<220> FEATURE:
<223> OTHER INFORMATION: Laboratory generated variant encoding a human
      beta-glucuronidase mutant, E1-S

<400> SEQUENCE: 1
ggggcccagc cggccctgca gggcgggatg ctgtaccccc aggagagccc gtcgcgggag        60
tgcaaggagc tggacggcct ctggagcttc gcgccgact tctctgacaa ccgacgccgg        120
ggcttcgagg agcagtggta ccggcggccg ctgtgggagt caggccccac cgtggacatg       180
ccagttccct ccagcttcaa tgacatcagc caggactggc gtctgcggca ttttgtcggc       240
tgggtgtggt acgaacggga ggtgatcctg ccggagcgat ggacccagga cctgcgcaca       300
agagtggtgc tgaggattgg cagtgcccat tcctatgcca tcgtgtgggt gaatggggtg       360
gacacgctag agcatgaggg gggctacctc cccttcgagg ccgacatcag caacctggtc       420
caggtggggc ccctgccctc ccggctccga atcactatcg ccatcaacaa cacactcacc       480
cccaccaccc tgccaccagg gaccatccaa tacctgactg acacctccaa gtatcccaag       540
ggttactttg tccagaacac atattttgac tttttcaact acgctggact gcagcggtct       600
gtacttctgt acacgacacc caccacctac atcgatgaca tcaccgtcac caccagcgtg       660
gagcaagaca gtgggctggt gaattaccag atctctgtca agggcagtaa cctgttcaag       720
ttggaagtgc gtcttttgga tgcagaaaac aaagtcgtgg cgaatgggac tgggacccag       780
ggccaactta aggtgccagg tgtcagcctc tggtggccgt acctgatgca cgaacgccct       840
gcctatctgt attcattgga ggtgcagctg actgcacaga cgtcactggg gcctgtgtct       900
gacttctaca cactccctgt ggggatccgc actgtggctg tcaccaagag ccagttcctc       960
atcaatggga aacctttcta tttccacggt gtcaacaagc atgaggatgc ggacatccga      1020
gggaagggct tcgactggcc gctgctggtg aaggacttca acctgcttcg ctggcttggt      1080
gccaacgctt tccgtaccag ccactacccc tatgcagagg aagtgatgca gatgtgtgac      1140
cgctatggga ttgtggtcat cgatgagtgt cccggcgtgg cctggcgct gccgcagttc      1200 ttcaacaacg tttctctgca tcaccacatg caggtgatgg aagaagtggt gcgtagggac      1260
aagaaccacc ccgcggtcgt gatgtggtct gtggccaacg agcctgcgtc ccacctagaa      1320
tctgctggct actacttgaa gatggtgatc gctcacacca aatccttgga ccccctcccgg      1380 cctgtgacct ttgtgagcaa ctctaactat gcagcagaca gggggctcc gtatgtggat      1440 gtgatctgtt tgaacagcta ctactcttgg tatcacgact acgggcacct ggagttgatt      1500
cagctgcagc tggccaccca gtttgagaac tggtataaga agatcagaa gcccattatt      1560
```

```
cagagcgagt atggagcaga atcgattgca gggtttcacc aggatccacc tctgatgttc    1620
actgaagagt accagaaaag tctgctagag cagtaccatc tgggtctgga tcaaaaacgc    1680
agaaaatatg tggttggaga gctcatttgg aattttgccg atttcatgac tgaacagtca    1740
ccgacgagag tgctggggaa taaaaagggg atcttcactc ggcagagaca accaaaaagt    1800
gcagcgttcc ttttgcgaga gagatactgg aagattgcca atgaaaccag gtatccccac    1860
tcagtagcca agtcacaatg tttggaaaac agcccgttta cttccgtcga c             1911

<210> SEQ ID NO 2
<211> LENGTH: 1911
<212> TYPE: DNA
<213> ORGANISM: Artificial Sequence
<220> FEATURE:
<223> OTHER INFORMATION: Laboratory generated variant encoding a human
      beta-glucuronidase mutant, E1-G

<400> SEQUENCE: 2
ggggcccagc cggccctgca gggcgggatg ctgtaccccc aggagagccc gtcgcgggag      60
tgcaaggagc tggacggcct ctggagcttc cgcgccgact ctctgacaa ccgacgccgg     120 ggcttcgagg agcagtggta ccggcggccg ctgtgggagt caggccccac cgtggacatg     180
ccagttccct ccagcttcaa tgacatcagc caggactggc gtctgcggca ttttgtcggc     240
tgggtgtggt acgaacggga ggtgatcctg ccggagcgat ggaccccagga cctgcgcaca     300 agagtggtgc tgaggattgg cagtgcccat tcctatgcca tcgtgtgggt gaatggggtg     360
gacacgctag agcatgaggg gggctacctc cccttcgagg ccgacatcag caacctggtc     420
caggtggggc ccctgccctc ccggctccga atcactatcg ccatcaacaa cacactcacc     480
cccaccaccc tgccaccagg gaccatccaa tacctgactg acacctccaa gtatcccaag     540
ggttactttg tccagaacac atattttgac ttttttcaact acgctggact gcagcggtct     600
gtacttctgt acacgacacc caccacctac atcgatgaca tcaccgtcac caccagcgtg     660
gagcaagaca gtgggctggt gaattaccag atctctgtca agggcagtaa cctgttcaag     720
ttggaagtgc gtcttttgga tgcagaaaac aaagtcgtgg cgaatgggac tgggacccag     780
ggccaactta aggtgccagg tgtcagcctc tggtggccgt acctgatgca cgaacgccct     840
gcctatctgt attcattgga ggtgcagctg actgcacaga cgtcactggg gcctgtgtct     900
gacttctaca cactccctgt ggggatccgc actgtggctg tcaccaagag ccagttcctc     960
atcaatggga aacctttcta tttccacggt gtcaacaagc atgaggatgc ggacatccga    1020
gggaagggct cgactggcc gctgctggtg aaggacttca acctgcttcg ctggcttggt    1080
gccaacgctt tccgtaccag ccactacccc tatgcagagg aagtgatgca gatgtgtgac    1140
cgctatggga ttgtggtcat cgatgagtgt cccggcgtgg gcctggcgct gccgcagttc    1200
ttcaacaacg tttctctgca tcaccacatg caggtgatgg aagaagtggt gcgtagggac    1260
aagaaccacc ccgcggtcgt gatgtggtct gtggccaacg agcctgcgtc ccacctagaa    1320
tctgctggct actacttgaa gatggtgatc gctcacacca atccttgga ccctcccgg     1380 cctgtgacct ttgtgagcaa ctctaactat gcagcagaca agggggctcc gtatgtggat    1440
gtgatctgtt tgaacagcta ctactcttgg tatcacgact acgggcacct ggagttgatt    1500
cagctgcagc tggccaccca gtttgagaac tggtataaga agtatcagaa gcccattatt    1560
cagagcgagt atggagcaga aggcattgca gggtttcacc aggatccacc tctgatgttc    1620
actgaagagt accagaaaag tctgctagag cagtaccatc tgggtctgga tcaaaaacgc    1680
```

```
agaaaatatg tggttggaga gctcatttgg aattttgccg atttcatgac tgaacagtca    1740
ccgacgagag tgctggggaa taaaaggggg atcttcactc ggcagagaca accaaaaagt    1800
gcagcgttcc ttttgcgaga gagatactgg aagattgcca atgaaaccag gtatccccac    1860
tcagtagcca agtcacaatg tttggaaaac agcccgttta cttccgtcga c             1911
```

<210> SEQ ID NO 3
<211> LENGTH: 1911
<212> TYPE: DNA
<213> ORGANISM: Artificial Sequence
<220> FEATURE:
<223> OTHER INFORMATION: Laboratory generated variant encoding a human
      beta-glucuronidase mutant, S2

<400> SEQUENCE: 3

```
gcggcccagc cggccctgca gggcgggatg ctgtacccccc aggagagccc gtcgcgggag      60
tgcaaggagc tggacggcct ctggagcttc cgcgccgact tctctgacaa ccgacgccgg     120
ggcttcgagg agcagtggta ccggcggccg ctgtgggagt caggccccac cgtggacatg     180
ccagttccct ccagcttcaa tgacatcagc caggactggc gtctgcggca ttttgtcggc     240
tgggtgtggt acgaacggga ggtgatcctg ccggagcgat ggaccccagga cctgcgcaca     300 agagtggtgc tgaggattgg cagtgcccat cctatgcca tcgtgtgggt aatggggtg      360 gacacgctag agcatgaggg gggctacctc cccttcgagg ccgacatcag caacctggtc    420
cagatggggc ccctgcccctc ccggctccga atcactatcg ccatcaacaa cacactcacc    480
cccaccaccc tgccaccagg gaccatccaa tacctgactg cacaccccaa gtatcccaag    540
ggttactttg tccagaacac atattttgac ttttttcaact acgctggact gcagcggtct    600
gtacttctgt acacgacacc caccacctac atcgatgaca tcaccgtcac caccagcgtg    660
gagcaagaca gtgggctggt gaattaccag atctctgtca agggcagtaa cctgttcaag    720
ttggaagtgc gtcttttgga tgcagaaaac aaagtcgtgg cgaatgggac tgggaccccag    780 ggccaactta aggtgccagg tgtcagcctc tggtggccgt acctgatgca cgaacgccct    840
gcctatctgt attcattgga ggtgcagctg actgcacaga cgtcactggg gcctgtgtct    900
gacttctaca cactccctgt ggggatccgc actgtggctg tcaccaagag ccagttcctc    960
atcaatggga aacctttcta tttccacggt gtcaacaagc atgaggatgc ggacatccga    1020
gggaagggct cgactggcc gctgctggtg aaggacttca acctgcttcg ctggcttggt    1080
gccaacgctt tccgtaccag ccactacccc tatgcagagg aagtgatgca gatgtgtgac    1140
cgctatggga ttgtggtcat cgatgagtgt cccggcgtgg gcctggcgct gccgcagttc    1200
ttcaacaacg tttctctgca tcaccacatg caggtgatgg aagaagtggt gcgtagggac    1260
aagaaccacc ccgcggtcgt gatgtggtct gtggccaacg agcctgcgtc ccacctagaa    1320
tctgctggct actacttgaa gatggtgatc gctcacacca atcccttgga ccccctcccgg    1380 cctgtgacct ttgtgagcaa ctctaactat gcagcagaca aggggggctcc gtatgtggat    1440 gtgatctgtt tgaacagcta ctactcttgg tatcacgact acgggcacct ggagttgatt    1500
cagctgcagc tggccaccca gtttgagaac tggtataaga agtatcagaa gcccattatt    1560
cagagcgagt atggagcaga atcgattgca gggtttcacc aggatccacc tctgatgttc    1620
actgaagagt accagaaaag tctgctagag cagtaccatc tgggtctgga tcaaaaacgc    1680
agaaaatatg tggttggaga gctcatttgg aattttgccg atttcatgac tttgcagtca    1740
ccgttgagag tgctggggaa taaaaggggg atcttcactc ggcagagaca accaaaaagt    1800
gcagcgttcc ttttgcgaga gagatactgg aagattgcca atgaaaccag gtatccccac    1860
```

```
tcagtagcca agtcacaatg tttggaaaac agcccgttta cttccgtcga c        1911
```

<210> SEQ ID NO 4
<211> LENGTH: 1911
<212> TYPE: DNA
<213> ORGANISM: Artificial Sequence
<220> FEATURE:
<223> OTHER INFORMATION: Laboratory generated variant encoding a human
      beta-glucuronidase mutant, S28

<400> SEQUENCE: 4

```
gcggcccagc cggccctgca gggcgggatg ctgtacccccc aggagagccc gtcgcgggag    60
tgcaaggagc tggacggcct ctggagcttc cgcgccgact tctctgacaa ccgacgccgg   120
ggcttcgagg agcagtggta ccggcggccg ctgtgggagt caggccccac cgtgacatg    180
ccagttccct ccagcttcaa tgacatcagc caggactggc gtctgcggca ttttgtcggc   240
tgggtgtggt acgaacggga ggtgatcctg ccggagcgat ggacccagga cctgcgcaca   300
agagtggtgc tgaggattgg cagtgcccat tcctatgcca tcgtgtgggt gaatggggtg   360
gacacgctag agcatgaggg gggctacctc cccttcgagg ccgacatcag caacctggtc   420
caggtggggc ccctgccctc ccggctccga atcactatcg ccatcaacaa cacactcacc   480
cccaccaccc tgccaccagg gaccatccaa tacctgactg acacctccaa gtatcccaag   540
ggttactttg tccagaacac atattttgac ttttttcaact acgctggact gcagcggtct   600
gtacttctgt acacgacacc caccacctac atcgatgaca tcaccgtcac caccagcgtg   660
gagcaagaca gtgggctggt gaattaccag atctctgtca agggcagtaa cctgttcaag   720
ttggaagtgc gtcttttgga tgcagaaaac aaagtcgtgg cgaatgggac tgggaccccag   780
ggccaactta aggtgccagg tgtcagcctc tggtggccgt acctgatgca cgaacgccct   840
gcctatctgt attcattgga ggtgcagctg actgcacaga cgtcactggg gcctgtgtct   900
gacttctaca cactccctgt ggggatccgc actgtggctg tcaccaagag ccagttcctc   960
atcaatggga aacctttcta tttccacggt gtcaacaagc atgaggatgc ggacatccga  1020
gggaagggct tcgactggcc gctgctggtg aaggacttca acctgcttcg ctggcttggt  1080
gccaacgctt tccgtaccag ccactacccc tatgcagagg aagtgatgca gatgtgtgac  1140
cgctatggga ttgtggtcat cgatgagtgt cccggcgtgg gctggcgct gccgcagttc  1200
ttcaacaacg tttctctgca tcaccacatg caggtgatgg aagaagtggt gcgtagggac  1260
aagaaccacc ccgcggtcgt gatgtggtct gtggccaacg agcctgcgtc ccacctagaa  1320
tctgctggct actacttgaa gatggtgatc gctcacacca aatccttgga cccctcccgg  1380
cctgtgacct ttgtgagcaa ctctaactat gcagcagaca agggggctcc gtatgtggat  1440
gtgatctgtt tgaacagcta ctactcttgg tatcacgact acgggcacct ggagttgatt  1500
cggctgcagc tggccaccca gtttgagaac tggtataaga agtatcagaa gcccattatt  1560
cagagcgagt atggagcaga atcgattgca gggtttcacc aggatccacc tctgatgttc  1620
actgaagagt accagaaaag tctgctagag cagtaccatc tgggtctgga tcaaaaacgc  1680
agaaaatatg tggttggaga gctcatttgg aattttgccg atttcatgac ttaccagtca  1740
ccgttcagag tgctggggaa taaaaagggg atcttcactc ggcagagaca accaaaaagt  1800
gcagcgttcc ttttgcgaga gagatactgg aagattgcca atgaaaccag gtatcccac   1860
tcagtagcca agtcacaatg tttggaaaac agcccgttta cttccgtcga c           1911
```

<210> SEQ ID NO 5

<211> LENGTH: 1911
<212> TYPE: DNA
<213> ORGANISM: Artificial Sequence
<220> FEATURE:
<223> OTHER INFORMATION: Laboratory generated variant encoding a human
      beta-glucuronidase mutant, E2-20

<400> SEQUENCE: 5

```
gcggcccagc cggccctgca gggcgggatg ctgtaccccc aggagagccc gtcgcgggag    60
tgcaaggagc tggacggcct ctggagcttc cgcgccgact tctctgacaa ccgacgccgg   120
ggcttcgagg agcagtggta ccggcggccg ctgtgggagt caggccccac cgtggacatg   180
ccagttccct ccagcttcaa tgacatcagc caggactggc gtctgcggca ttttgtcggc   240
tgggtgtggt acgaacggga ggtgatcctg ccggagcgat ggaccccagga cctgcgcaca   300
agagtggtgc tgaggattgg cagtgcccat tcctatgcca tcgtgtgggt gaatggggtg   360
gacacgctag agcatgaggg gggctacctc cccttcgagg ccgacatcag caacctggtc   420
caggtgggc ccctgccctc ccggctccga atcactatcg ccatcaacaa cacactcacc   480
cccaccaccc tgccaccagg gaccatccaa tacctgactg acacctccaa gtatcccaag   540
ggttactttg tccagaacac atattttgac tttttcaact acgctggact gcagcggtct   600
gtacttctgt acacgacacc caccacctac atcgatgaca tcaccgtcac caccagcgtg   660
gagcaagaca gtgggcaggt gaattaccag atctctgtca agggcagtaa ccagttcaag   720
ttggaagtgc gtcttttaga tgcagaaaac aaagtcgtgg cgaatgggac tgggacccag   780
ggccaactta aggtgccagg tgtcagcctc tggtggccgt acctgatgca cgaacgccct   840
gcctatctgt attcattgga ggtgcagctg actgcacaga cgtcactggg gcctgtgtct   900
gacttctaca cactccctgt ggggatccga actgtggctg tcaccaagag ccagttcctc   960
atcaatggga aacctttcta tttccacggt gtcaacaagc atgaggatgc ggacatccga  1020
gggaagggct cgactggcc gctgctggtg aaggacttca acctgcttcg ctggcttggt  1080
gccaacgctt tccgtaccag ccactacccc tatgcagagg aagtgatgca gatgtgtgac  1140
cgctatggga ttgtggtcat cgatgagtgt cccggcgtgg gctggcgct gccgcagttc  1200
ttcaacaacg tttctctgca tcaccacatg caggtgatgg aagaagtggt gcgtagggac  1260
aagaaccacc ccgcggtcgt gatgtggtct gtggccaacg agcctgcgtc ccacctagaa  1320
tctgctggct actacttgaa gatggtgatc gctcacacca atccttgga ccctcccgg    1380
cctgtgacct tgtgagcaa ctctaactat gcagcagaca aggggctcc gtatgtggat  1440
gtgatctgtt tgaacagcta ctactcttgg tatcacgact acgggcacct ggagttgatt  1500
cagctgcagc tggccaccca gtttgagaac tggtataaga agtatcagaa gcccattatt  1560
cagagcgagt atggagcaga aggcattgca gggtttcacc aggatccacc tctgatgttc  1620
actgaagagt accagaaaag tctgctagag cagtaccatc tgggtctgga tcaaaaacgc  1680
agaaaatatg tggttggaga gctcatttgg aattttgccg atttcatgac tgaacagtca  1740
ccgacgagag tgctgggaa taaaagggg atcttcactc ggcagagaca accaaaaagt  1800
gcagcgttcc ttttgcgaga gagatactgg aagattgcca atgaaaccag gtatccccac  1860
tcagtagcca agtcacaatg tttggaaaac agcccgttta cttccgtcga c           1911
```

<210> SEQ ID NO 6
<211> LENGTH: 637
<212> TYPE: PRT
<213> ORGANISM: Artificial Sequence
<220> FEATURE:
<223> OTHER INFORMATION: Laboratory generated variant, E1-S, based upon -continued the human beta-glucuronidase

<400> SEQUENCE: 6

Gly Ala Gln Pro Ala Leu Gln Gly Gly Met Leu Tyr Pro Gln Glu Ser
1               5                   10                  15

Pro Ser Arg Glu Cys Lys Glu Leu Asp Gly Leu Trp Ser Phe Arg Ala
            20                  25                  30

Asp Phe Ser Asp Asn Arg Arg Gly Phe Glu Glu Gln Trp Tyr Arg
            35                  40                  45

Arg Pro Leu Trp Glu Ser Gly Pro Thr Val Asp Met Pro Val Pro Ser
        50                  55                  60

Ser Phe Asn Asp Ile Ser Gln Asp Trp Arg Leu Arg His Phe Val Gly
65                  70                  75                  80

Trp Val Trp Tyr Glu Arg Glu Val Ile Leu Pro Glu Arg Trp Thr Gln
                85                  90                  95

Asp Leu Arg Thr Arg Val Val Leu Arg Ile Gly Ser Ala His Ser Tyr
            100                 105                 110

Ala Ile Val Trp Val Asn Gly Val Asp Thr Leu Glu His Glu Gly Gly
            115                 120                 125

Tyr Leu Pro Phe Glu Ala Asp Ile Ser Asn Leu Val Gln Val Gly Pro
        130                 135                 140

Leu Pro Ser Arg Leu Arg Ile Thr Ile Ala Ile Asn Asn Thr Leu Thr
145                 150                 155                 160

Pro Thr Thr Leu Pro Pro Gly Thr Ile Gln Tyr Leu Thr Asp Thr Ser
                165                 170                 175

Lys Tyr Pro Lys Gly Tyr Phe Val Gln Asn Thr Tyr Phe Asp Phe Phe
            180                 185                 190

Asn Tyr Ala Gly Leu Gln Arg Ser Val Leu Leu Tyr Thr Thr Pro Thr
        195                 200                 205

Thr Tyr Ile Asp Asp Ile Thr Val Thr Thr Ser Val Glu Gln Asp Ser
210                 215                 220

Gly Leu Val Asn Tyr Gln Ile Ser Val Lys Gly Ser Asn Leu Phe Lys
225                 230                 235                 240

Leu Glu Val Arg Leu Leu Asp Ala Glu Asn Lys Val Val Ala Asn Gly
                245                 250                 255

Thr Gly Thr Gln Gly Gln Leu Lys Val Pro Gly Val Ser Leu Trp Trp
            260                 265                 270

Pro Tyr Leu Met His Glu Arg Pro Ala Tyr Leu Tyr Ser Leu Glu Val
        275                 280                 285

Gln Leu Thr Ala Gln Thr Ser Leu Gly Pro Val Ser Asp Phe Tyr Thr
290                 295                 300

Leu Pro Val Gly Ile Arg Thr Val Ala Val Thr Lys Ser Gln Phe Leu
305                 310                 315                 320

Ile Asn Gly Lys Pro Phe Tyr Phe His Gly Val Asn Lys His Glu Asp
                325                 330                 335

Ala Asp Ile Arg Gly Lys Gly Phe Asp Trp Pro Leu Leu Val Lys Asp
            340                 345                 350

Phe Asn Leu Leu Arg Trp Leu Gly Ala Asn Ala Phe Arg Thr Ser His
        355                 360                 365

Tyr Pro Tyr Ala Glu Glu Val Met Gln Met Cys Asp Arg Tyr Gly Ile
        370                 375                 380

Val Val Ile Asp Glu Cys Pro Gly Val Gly Leu Ala Leu Pro Gln Phe
385                 390                 395                 400

Phe Asn Asn Val Ser Leu His His His Met Gln Val Met Glu Glu Val

```
                    405                 410                 415
Val Arg Arg Asp Lys Asn His Pro Ala Val Val Met Trp Ser Val Ala
            420                 425                 430

Asn Glu Pro Ala Ser His Leu Glu Ser Ala Gly Tyr Tyr Leu Lys Met
            435                 440                 445

Val Ile Ala His Thr Lys Ser Leu Asp Pro Ser Arg Pro Val Thr Phe
450                 455                 460

Val Ser Asn Ser Asn Tyr Ala Ala Asp Lys Gly Ala Pro Tyr Val Asp
465                 470                 475                 480

Val Ile Cys Leu Asn Ser Tyr Tyr Ser Trp Tyr His Asp Tyr Gly His
            485                 490                 495

Leu Glu Leu Ile Gln Leu Gln Leu Ala Thr Gln Phe Glu Asn Trp Tyr
            500                 505                 510

Lys Lys Tyr Gln Lys Pro Ile Ile Gln Ser Glu Tyr Gly Ala Glu Ser
            515                 520                 525

Ile Ala Gly Phe His Gln Asp Pro Pro Leu Met Phe Thr Glu Glu Tyr
            530                 535                 540

Gln Lys Ser Leu Leu Glu Gln Tyr His Leu Gly Leu Asp Gln Lys Arg
545                 550                 555                 560

Arg Lys Tyr Val Val Gly Glu Leu Ile Trp Asn Phe Ala Asp Phe Met
                565                 570                 575

Thr Glu Gln Ser Pro Thr Arg Val Leu Gly Asn Lys Lys Gly Ile Phe
            580                 585                 590

Thr Arg Gln Arg Gln Pro Lys Ser Ala Ala Phe Leu Leu Arg Glu Arg
            595                 600                 605

Tyr Trp Lys Ile Ala Asn Glu Thr Arg Tyr Pro His Ser Val Ala Lys
610                 615                 620

Ser Gln Cys Leu Glu Asn Ser Pro Phe Thr Ser Val Asp
625                 630                 635

<210> SEQ ID NO 7
<211> LENGTH: 637
<212> TYPE: PRT
<213> ORGANISM: Artificial Sequence
<220> FEATURE:
<223> OTHER INFORMATION: Laboratory generated variant, E1-G, based upon
      the human beta-glucuronidase

<400> SEQUENCE: 7

Gly Ala Gln Pro Ala Leu Gln Gly Gly Met Leu Tyr Pro Gln Glu Ser
1               5                   10                  15

Pro Ser Arg Glu Cys Lys Glu Leu Asp Gly Leu Trp Ser Phe Arg Ala
            20                  25                  30

Asp Phe Ser Asp Asn Arg Arg Gly Phe Glu Gln Trp Tyr Arg
        35                  40                  45

Arg Pro Leu Trp Glu Ser Gly Pro Thr Val Asp Met Pro Val Pro Ser
50                  55                  60

Ser Phe Asn Asp Ile Ser Gln Asp Trp Arg Leu Arg His Phe Val Gly
65                  70                  75                  80

Trp Val Trp Tyr Glu Arg Glu Val Ile Leu Pro Glu Arg Trp Thr Gln
                85                  90                  95

Asp Leu Arg Thr Arg Val Val Leu Arg Ile Gly Ser Ala His Ser Tyr
            100                 105                 110

Ala Ile Val Trp Val Asn Gly Val Asp Thr Leu Glu His Glu Gly Gly
            115                 120                 125

Tyr Leu Pro Phe Glu Ala Asp Ile Ser Asn Leu Val Gln Val Gly Pro
```

-continued

```
              130                 135                 140
Leu Pro Ser Arg Leu Arg Ile Thr Ile Ala Ile Asn Asn Thr Leu Thr
145                 150                 155                 160

Pro Thr Thr Leu Pro Pro Gly Thr Ile Gln Tyr Leu Thr Asp Thr Ser
                165                 170                 175

Lys Tyr Pro Lys Gly Tyr Phe Val Gln Asn Thr Tyr Phe Asp Phe Phe
            180                 185                 190

Asn Tyr Ala Gly Leu Gln Arg Ser Val Leu Leu Tyr Thr Thr Pro Thr
            195                 200                 205

Thr Tyr Ile Asp Asp Ile Thr Val Thr Thr Ser Val Glu Gln Asp Ser
210                 215                 220

Gly Leu Val Asn Tyr Gln Ile Ser Val Lys Gly Ser Asn Leu Phe Lys
225                 230                 235                 240

Leu Glu Val Arg Leu Leu Asp Ala Glu Asn Lys Val Val Ala Asn Gly
                245                 250                 255

Thr Gly Thr Gln Gly Gln Leu Lys Val Pro Gly Val Ser Leu Trp Trp
                260                 265                 270

Pro Tyr Leu Met His Glu Arg Pro Ala Tyr Leu Tyr Ser Leu Glu Val
            275                 280                 285

Gln Leu Thr Ala Gln Thr Ser Leu Gly Pro Val Ser Asp Phe Tyr Thr
290                 295                 300

Leu Pro Val Gly Ile Arg Thr Val Ala Val Thr Lys Ser Gln Phe Leu
305                 310                 315                 320

Ile Asn Gly Lys Pro Phe Tyr Phe His Gly Val Asn Lys His Glu Asp
                325                 330                 335

Ala Asp Ile Arg Gly Lys Gly Phe Asp Trp Pro Leu Leu Val Lys Asp
                340                 345                 350

Phe Asn Leu Leu Arg Trp Leu Gly Ala Asn Ala Phe Arg Thr Ser His
            355                 360                 365

Tyr Pro Tyr Ala Glu Glu Val Met Gln Met Cys Asp Arg Tyr Gly Ile
370                 375                 380

Val Val Ile Asp Glu Cys Pro Gly Val Gly Leu Ala Leu Pro Gln Phe
385                 390                 395                 400

Phe Asn Asn Val Ser Leu His His Met Gln Val Met Glu Glu Val
            405                 410                 415

Val Arg Arg Asp Lys Asn His Pro Ala Val Val Met Trp Ser Val Ala
                420                 425                 430

Asn Glu Pro Ala Ser His Leu Glu Ser Ala Gly Tyr Tyr Leu Lys Met
            435                 440                 445

Val Ile Ala His Thr Lys Ser Leu Asp Pro Ser Arg Pro Val Thr Phe
450                 455                 460

Val Ser Asn Ser Asn Tyr Ala Ala Asp Lys Gly Ala Pro Tyr Val Asp
465                 470                 475                 480

Val Ile Cys Leu Asn Ser Tyr Tyr Ser Trp Tyr His Asp Tyr Gly His
                485                 490                 495

Leu Glu Leu Ile Gln Leu Gln Leu Ala Thr Gln Phe Glu Asn Trp Tyr
            500                 505                 510

Lys Lys Tyr Gln Lys Pro Ile Ile Gln Ser Glu Tyr Gly Ala Glu Gly
            515                 520                 525

Ile Ala Gly Phe His Gln Asp Pro Pro Leu Met Phe Thr Glu Glu Tyr
            530                 535                 540

Gln Lys Ser Leu Leu Glu Gln Tyr His Leu Gly Leu Asp Gln Lys Arg
545                 550                 555                 560
```

```
Arg Lys Tyr Val Val Gly Glu Leu Ile Trp Asn Phe Ala Asp Phe Met
            565                 570                 575

Thr Glu Gln Ser Pro Thr Arg Val Leu Gly Asn Lys Lys Gly Ile Phe
        580                 585                 590

Thr Arg Gln Arg Gln Pro Lys Ser Ala Ala Phe Leu Leu Arg Glu Arg
        595                 600                 605

Tyr Trp Lys Ile Ala Asn Glu Thr Arg Tyr Pro His Ser Val Ala Lys
        610                 615                 620

Ser Gln Cys Leu Glu Asn Ser Pro Phe Thr Ser Val Asp
625                 630                 635

<210> SEQ ID NO 8
<211> LENGTH: 637
<212> TYPE: PRT
<213> ORGANISM: Artificial Sequence
<220> FEATURE:
<223> OTHER INFORMATION: Laboratory generated variant, S2, based upon
      the human beta-glucuronidase

<400> SEQUENCE: 8

Ala Ala Gln Pro Ala Leu Gln Gly Gly Met Leu Tyr Pro Gln Glu Ser
1               5                   10                  15

Pro Ser Arg Glu Cys Lys Glu Leu Asp Gly Leu Trp Ser Phe Arg Ala
            20                  25                  30

Asp Phe Ser Asp Asn Arg Arg Gly Phe Glu Gln Trp Tyr Arg
        35                  40                  45

Arg Pro Leu Trp Glu Ser Gly Pro Thr Val Asp Met Pro Val Pro Ser
    50                  55                  60

Ser Phe Asn Asp Ile Ser Gln Asp Trp Arg Leu Arg His Phe Val Gly
65              70                  75                  80

Trp Val Trp Tyr Glu Arg Glu Val Ile Leu Pro Glu Arg Trp Thr Gln
                85                  90                  95

Asp Leu Arg Thr Arg Val Val Leu Arg Ile Gly Ser Ala His Ser Tyr
            100                 105                 110

Ala Ile Val Trp Val Asn Gly Val Asp Thr Leu Glu His Glu Gly Gly
        115                 120                 125

Tyr Leu Pro Phe Glu Ala Asp Ile Ser Asn Leu Val Gln Met Gly Pro
    130                 135                 140

Leu Pro Ser Arg Leu Arg Ile Thr Ile Ala Ile Asn Asn Thr Leu Thr
145                 150                 155                 160

Pro Thr Thr Leu Pro Pro Gly Thr Ile Gln Tyr Leu Thr Asp Thr Ser
                165                 170                 175

Lys Tyr Pro Lys Gly Tyr Phe Val Gln Asn Thr Tyr Phe Asp Phe Phe
            180                 185                 190

Asn Tyr Ala Gly Leu Gln Arg Ser Val Leu Leu Tyr Thr Thr Pro Thr
        195                 200                 205

Thr Tyr Ile Asp Asp Ile Thr Val Thr Thr Ser Val Glu Gln Asp Ser
    210                 215                 220

Gly Leu Val Asn Tyr Gln Ile Ser Val Lys Gly Ser Asn Leu Phe Lys
225                 230                 235                 240

Leu Glu Val Arg Leu Leu Asp Ala Glu Asn Lys Val Val Ala Asn Gly
                245                 250                 255

Thr Gly Thr Gln Gly Gln Leu Lys Val Pro Gly Val Ser Leu Trp Trp
            260                 265                 270

Pro Tyr Leu Met His Glu Arg Pro Ala Tyr Leu Tyr Ser Leu Glu Val
        275                 280                 285
```

-continued

```
Gln Leu Thr Ala Gln Thr Ser Leu Gly Pro Val Ser Asp Phe Tyr Thr
    290                 295                 300

Leu Pro Val Gly Ile Arg Thr Val Ala Val Thr Lys Ser Gln Phe Leu
305                 310                 315                 320

Ile Asn Gly Lys Pro Phe Tyr Phe His Gly Val Asn Lys His Glu Asp
                325                 330                 335

Ala Asp Ile Arg Gly Lys Gly Phe Asp Trp Pro Leu Leu Val Lys Asp
            340                 345                 350

Phe Asn Leu Leu Arg Trp Leu Gly Ala Asn Ala Phe Arg Thr Ser His
        355                 360                 365

Tyr Pro Tyr Ala Glu Glu Val Met Gln Met Cys Asp Arg Tyr Gly Ile
    370                 375                 380

Val Val Ile Asp Glu Cys Pro Gly Val Gly Leu Ala Leu Pro Gln Phe
385                 390                 395                 400

Phe Asn Asn Val Ser Leu His His Met Gln Val Met Glu Glu Val
                405                 410                 415

Val Arg Arg Asp Lys Asn His Pro Ala Val Val Met Trp Ser Val Ala
            420                 425                 430

Asn Glu Pro Ala Ser His Leu Glu Ser Ala Gly Tyr Tyr Leu Lys Met
        435                 440                 445

Val Ile Ala His Thr Lys Ser Leu Asp Pro Ser Arg Pro Val Thr Phe
    450                 455                 460

Val Ser Asn Ser Asn Tyr Ala Ala Asp Lys Gly Ala Pro Tyr Val Asp
465                 470                 475                 480

Val Ile Cys Leu Asn Ser Tyr Tyr Ser Trp Tyr His Asp Tyr Gly His
                485                 490                 495

Leu Glu Leu Ile Gln Leu Gln Leu Ala Thr Gln Phe Glu Asn Trp Tyr
            500                 505                 510

Lys Lys Tyr Gln Lys Pro Ile Ile Gln Ser Glu Tyr Gly Ala Glu Ser
        515                 520                 525

Ile Ala Gly Phe His Gln Asp Pro Pro Leu Met Phe Thr Glu Glu Tyr
    530                 535                 540

Gln Lys Ser Leu Leu Glu Gln Tyr His Leu Gly Leu Asp Gln Lys Arg
545                 550                 555                 560

Arg Lys Tyr Val Val Gly Glu Leu Ile Trp Asn Phe Ala Asp Phe Met
                565                 570                 575

Thr Leu Gln Ser Pro Leu Arg Val Leu Gly Asn Lys Lys Gly Ile Phe
            580                 585                 590

Thr Arg Gln Arg Gln Pro Lys Ser Ala Ala Phe Leu Leu Arg Glu Arg
        595                 600                 605

Tyr Trp Lys Ile Ala Asn Glu Thr Arg Tyr Pro His Ser Val Ala Lys
    610                 615                 620

Ser Gln Cys Leu Glu Asn Ser Pro Phe Thr Ser Val Asp
625                 630                 635

<210> SEQ ID NO 9
<211> LENGTH: 637
<212> TYPE: PRT
<213> ORGANISM: Artificial Sequence
<220> FEATURE:
<223> OTHER INFORMATION: Laboratory generated variant, S28, based upon
      the human beta-glucuronidase

<400> SEQUENCE: 9

Ala Ala Gln Pro Ala Leu Gln Gly Gly Met Leu Tyr Pro Gln Glu Ser
1               5                   10                  15
```

```
Pro Ser Arg Glu Cys Lys Glu Leu Asp Gly Leu Trp Ser Phe Arg Ala
        20                  25                  30
Asp Phe Ser Asp Asn Arg Arg Gly Phe Glu Gln Trp Tyr Arg
    35                  40                  45
Arg Pro Leu Trp Glu Ser Gly Pro Thr Val Asp Met Pro Val Pro Ser
        50                  55                  60
Ser Phe Asn Asp Ile Ser Gln Asp Trp Arg Leu Arg His Phe Val Gly
65                  70                  75                  80
Trp Val Trp Tyr Glu Arg Glu Val Ile Leu Pro Glu Arg Trp Thr Gln
                85                  90                  95
Asp Leu Arg Thr Arg Val Val Leu Arg Ile Gly Ser Ala His Ser Tyr
            100                 105                 110
Ala Ile Val Trp Val Asn Gly Val Asp Thr Leu Glu His Glu Gly Gly
        115                 120                 125
Tyr Leu Pro Phe Glu Ala Asp Ile Ser Asn Leu Val Gln Val Gly Pro
        130                 135                 140
Leu Pro Ser Arg Leu Arg Ile Thr Ile Ala Ile Asn Asn Thr Leu Thr
145                 150                 155                 160
Pro Thr Thr Leu Pro Pro Gly Thr Ile Gln Tyr Leu Thr Asp Thr Ser
                165                 170                 175
Lys Tyr Pro Lys Gly Tyr Phe Val Gln Asn Thr Tyr Phe Asp Phe Phe
            180                 185                 190
Asn Tyr Ala Gly Leu Gln Arg Ser Val Leu Leu Tyr Thr Thr Pro Thr
        195                 200                 205
Thr Tyr Ile Asp Asp Ile Thr Val Thr Thr Ser Val Glu Gln Asp Ser
    210                 215                 220
Gly Leu Val Asn Tyr Gln Ile Ser Val Lys Gly Ser Asn Leu Phe Lys
225                 230                 235                 240
Leu Glu Val Arg Leu Leu Asp Ala Glu Asn Lys Val Val Ala Asn Gly
                245                 250                 255
Thr Gly Thr Gln Gly Gln Leu Lys Val Pro Gly Val Ser Leu Trp Trp
            260                 265                 270
Pro Tyr Leu Met His Glu Arg Pro Ala Tyr Leu Tyr Ser Leu Glu Val
        275                 280                 285
Gln Leu Thr Ala Gln Thr Ser Leu Gly Pro Val Ser Asp Phe Tyr Thr
    290                 295                 300
Leu Pro Val Gly Ile Arg Thr Val Ala Val Thr Lys Ser Gln Phe Leu
305                 310                 315                 320
Ile Asn Gly Lys Pro Phe Tyr Phe His Gly Val Asn Lys His Glu Asp
                325                 330                 335
Ala Asp Ile Arg Gly Lys Gly Phe Asp Trp Pro Leu Leu Val Lys Asp
            340                 345                 350
Phe Asn Leu Leu Arg Trp Leu Gly Ala Asn Ala Phe Arg Thr Ser His
        355                 360                 365
Tyr Pro Tyr Ala Glu Glu Val Met Gln Met Cys Asp Arg Tyr Gly Ile
    370                 375                 380
Val Val Ile Asp Glu Cys Pro Gly Val Gly Leu Ala Leu Pro Gln Phe
385                 390                 395                 400
Phe Asn Asn Val Ser Leu His His Met Gln Val Met Glu Glu Val
                405                 410                 415
Val Arg Arg Asp Lys Asn His Pro Ala Val Val Met Trp Ser Val Ala
            420                 425                 430
Asn Glu Pro Ala Ser His Leu Glu Ser Ala Gly Tyr Tyr Leu Lys Met
        435                 440                 445
```

```
Val Ile Ala His Thr Lys Ser Leu Asp Pro Ser Arg Pro Val Thr Phe
    450                 455                 460

Val Ser Asn Ser Asn Tyr Ala Ala Asp Lys Gly Ala Pro Tyr Val Asp
465                 470                 475                 480

Val Ile Cys Leu Asn Ser Tyr Tyr Ser Trp Tyr His Tyr Gly His
                485                 490                 495

Leu Glu Leu Ile Arg Leu Gln Leu Ala Thr Gln Phe Glu Asn Trp Tyr
            500                 505                 510

Lys Lys Tyr Gln Lys Pro Ile Ile Gln Ser Glu Tyr Gly Ala Glu Ser
        515                 520                 525

Ile Ala Gly Phe His Gln Asp Pro Leu Met Phe Thr Glu Glu Tyr
    530                 535                 540

Gln Lys Ser Leu Leu Glu Gln Tyr His Leu Gly Leu Asp Gln Lys Arg
545                 550                 555                 560

Arg Lys Tyr Val Val Gly Glu Leu Ile Trp Asn Phe Ala Asp Phe Met
                565                 570                 575

Thr Tyr Gln Ser Pro Phe Arg Val Leu Gly Asn Lys Lys Gly Ile Phe
            580                 585                 590

Thr Arg Gln Arg Gln Pro Lys Ser Ala Ala Phe Leu Leu Arg Glu Arg
        595                 600                 605

Tyr Trp Lys Ile Ala Asn Glu Thr Arg Tyr Pro His Ser Val Ala Lys
    610                 615                 620

Ser Gln Cys Leu Glu Asn Ser Pro Phe Thr Ser Val Asp
625                 630                 635

<210> SEQ ID NO 10
<211> LENGTH: 637
<212> TYPE: PRT
<213> ORGANISM: Artificial Sequence
<220> FEATURE:
<223> OTHER INFORMATION: Laboratory generated variant, E2-20, based upon
      the human beta-glucuronidase

<400> SEQUENCE: 10

Ala Ala Gln Pro Ala Leu Gln Gly Gly Met Leu Tyr Pro Gln Glu Ser
1               5                   10                  15

Pro Ser Arg Glu Cys Lys Glu Leu Asp Gly Leu Trp Ser Phe Arg Ala
            20                  25                  30

Asp Phe Ser Asp Asn Arg Arg Gly Phe Glu Glu Gln Trp Tyr Arg
        35                  40                  45

Arg Pro Leu Trp Glu Ser Gly Pro Thr Val Asp Met Pro Val Pro Ser
50                  55                  60

Ser Phe Asn Asp Ile Ser Gln Asp Trp Arg Leu Arg His Phe Val Gly
65                  70                  75                  80

Trp Val Trp Tyr Glu Arg Glu Val Ile Leu Pro Glu Arg Trp Thr Gln
                85                  90                  95

Asp Leu Arg Thr Arg Val Val Leu Arg Ile Gly Ser Ala His Ser Tyr
            100                 105                 110

Ala Ile Val Trp Val Asn Gly Val Asp Thr Leu Glu His Glu Gly Gly
        115                 120                 125

Tyr Leu Pro Phe Glu Ala Asp Ile Ser Asn Leu Val Gln Val Gly Pro
    130                 135                 140

Leu Pro Ser Arg Leu Arg Ile Thr Ile Ala Ile Asn Asn Thr Leu Thr
145                 150                 155                 160

Pro Thr Thr Leu Pro Pro Gly Thr Ile Gln Tyr Leu Thr Asp Thr Ser
                165                 170                 175
```

```
Lys Tyr Pro Lys Gly Tyr Phe Val Gln Asn Thr Tyr Phe Asp Phe
                180                 185                 190

Asn Tyr Ala Gly Leu Gln Arg Ser Val Leu Leu Tyr Thr Thr Pro Thr
            195                 200                 205

Thr Tyr Ile Asp Asp Ile Thr Val Thr Thr Ser Val Glu Gln Asp Ser
        210                 215                 220

Gly Gln Val Asn Tyr Gln Ile Ser Val Lys Gly Ser Asn Gln Phe Lys
225                 230                 235                 240

Leu Glu Val Arg Leu Leu Asp Ala Glu Asn Lys Val Val Ala Asn Gly
                245                 250                 255

Thr Gly Thr Gln Gly Gln Leu Lys Val Pro Gly Val Ser Leu Trp Trp
            260                 265                 270

Pro Tyr Leu Met His Glu Arg Pro Ala Tyr Leu Tyr Ser Leu Glu Val
        275                 280                 285

Gln Leu Thr Ala Gln Thr Ser Leu Gly Pro Val Ser Asp Phe Tyr Thr
        290                 295                 300

Leu Pro Val Gly Ile Arg Thr Val Ala Val Thr Lys Ser Gln Phe Leu
305                 310                 315                 320

Ile Asn Gly Lys Pro Phe Tyr Phe His Gly Val Asn Lys His Glu Asp
                325                 330                 335

Ala Asp Ile Arg Gly Lys Gly Phe Asp Trp Pro Leu Leu Val Lys Asp
            340                 345                 350

Phe Asn Leu Leu Arg Trp Leu Gly Ala Asn Ala Phe Arg Thr Ser His
        355                 360                 365

Tyr Pro Tyr Ala Glu Glu Val Met Gln Met Cys Asp Arg Tyr Gly Ile
        370                 375                 380

Val Val Ile Asp Glu Cys Pro Gly Val Gly Leu Ala Leu Pro Gln Phe
385                 390                 395                 400

Phe Asn Asn Val Ser Leu His His Met Gln Val Met Glu Glu Val
                405                 410                 415

Val Arg Arg Asp Lys Asn His Pro Ala Val Val Met Trp Ser Val Ala
            420                 425                 430

Asn Glu Pro Ala Ser His Leu Glu Ser Ala Gly Tyr Tyr Leu Lys Met
        435                 440                 445

Val Ile Ala His Thr Lys Ser Leu Asp Pro Ser Arg Pro Val Thr Phe
        450                 455                 460

Val Ser Asn Ser Asn Tyr Ala Ala Asp Lys Gly Ala Pro Tyr Val Asp
465                 470                 475                 480

Val Ile Cys Leu Asn Ser Tyr Tyr Ser Trp Tyr His Asp Tyr Gly His
                485                 490                 495

Leu Glu Leu Ile Gln Leu Gln Leu Ala Thr Gln Phe Glu Asn Trp Tyr
            500                 505                 510

Lys Lys Tyr Gln Lys Pro Ile Ile Gln Ser Glu Tyr Gly Ala Glu Gly
        515                 520                 525

Ile Ala Gly Phe His Gln Asp Pro Pro Leu Met Phe Thr Glu Glu Tyr
        530                 535                 540

Gln Lys Ser Leu Leu Glu Gln Tyr His Leu Gly Leu Asp Gln Lys Arg
545                 550                 555                 560

Arg Lys Tyr Val Val Gly Glu Leu Ile Trp Asn Phe Ala Asp Phe Met
                565                 570                 575

Thr Glu Gln Ser Pro Thr Arg Val Leu Gly Asn Lys Lys Gly Ile Phe
            580                 585                 590

Thr Arg Gln Arg Gln Pro Lys Ser Ala Ala Phe Leu Leu Arg Glu Arg
```

-continued

```
                595                 600                 605
Tyr Trp Lys Ile Ala Asn Glu Thr Arg Tyr Pro His Ser Val Ala Lys
        610                 615                 620

Ser Gln Cys Leu Glu Asn Ser Pro Phe Thr Ser Val Asp
625                 630                 635

<210> SEQ ID NO 11
<211> LENGTH: 651
<212> TYPE: PRT
<213> ORGANISM: Homo sapiens

<400> SEQUENCE: 11

Met Ala Arg Gly Ser Ala Val Ala Trp Ala Leu Gly Pro Leu Leu
1               5                   10                  15

Trp Gly Cys Ala Leu Gly Leu Gln Gly Gly Met Leu Tyr Pro Gln Glu
            20                  25                  30

Ser Pro Ser Arg Glu Cys Lys Glu Leu Asp Gly Leu Trp Ser Phe Arg
        35                  40                  45

Ala Asp Phe Ser Asp Asn Arg Arg Gly Phe Glu Glu Gln Trp Tyr
    50                  55                  60

Arg Arg Pro Leu Trp Glu Ser Gly Pro Thr Val Asp Met Pro Val Pro
65                  70                  75                  80

Ser Ser Phe Asn Asp Ile Ser Gln Asp Trp Arg Leu Arg His Phe Val
                85                  90                  95

Gly Trp Val Trp Tyr Glu Arg Glu Val Ile Leu Pro Glu Arg Trp Thr
            100                 105                 110

Gln Asp Leu Arg Thr Arg Val Val Leu Arg Ile Gly Ser Ala His Ser
        115                 120                 125

Tyr Ala Ile Val Trp Val Asn Gly Val Asp Thr Leu Glu His Glu Gly
    130                 135                 140

Gly Tyr Leu Pro Phe Glu Ala Asp Ile Ser Asn Leu Val Gln Val Gly
145                 150                 155                 160

Pro Leu Pro Ser Arg Leu Arg Ile Thr Ile Ala Ile Asn Asn Thr Leu
                165                 170                 175

Thr Pro Thr Thr Leu Pro Pro Gly Thr Ile Gln Tyr Leu Thr Asp Thr
            180                 185                 190

Ser Lys Tyr Pro Lys Gly Tyr Phe Val Gln Asn Thr Tyr Phe Asp Phe
        195                 200                 205

Phe Asn Tyr Ala Gly Leu Gln Arg Ser Val Leu Leu Tyr Thr Thr Pro
    210                 215                 220

Thr Thr Tyr Ile Asp Asp Ile Thr Val Thr Thr Ser Val Glu Gln Asp
225                 230                 235                 240

Ser Gly Leu Val Asn Tyr Gln Ile Ser Val Lys Gly Ser Asn Leu Phe
                245                 250                 255

Lys Leu Glu Val Arg Leu Leu Asp Ala Glu Asn Lys Val Val Ala Asn
            260                 265                 270

Gly Thr Gly Thr Gln Gly Gln Leu Lys Val Pro Gly Val Ser Leu Trp
        275                 280                 285

Trp Pro Tyr Leu Met His Glu Arg Pro Ala Tyr Leu Tyr Ser Leu Glu
    290                 295                 300

Val Gln Leu Thr Ala Gln Thr Ser Leu Gly Pro Val Ser Asp Phe Tyr
305                 310                 315                 320

Thr Leu Pro Val Gly Ile Arg Thr Val Ala Val Thr Lys Ser Gln Phe
                325                 330                 335

Leu Ile Asn Gly Lys Pro Phe Tyr Phe His Gly Val Asn Lys His Glu
```

-continued

```
                340                 345                 350
Asp Ala Asp Ile Arg Gly Lys Gly Phe Asp Trp Pro Leu Leu Val Lys
            355                 360                 365
Asp Phe Asn Leu Leu Arg Trp Leu Gly Ala Asn Ala Phe Arg Thr Ser
        370                 375                 380
His Tyr Pro Tyr Ala Glu Glu Val Met Gln Met Cys Asp Arg Tyr Gly
385                 390                 395                 400
Ile Val Val Ile Asp Glu Cys Pro Gly Val Gly Leu Ala Leu Pro Gln
            405                 410                 415
Phe Phe Asn Asn Val Ser Leu His His His Met Gln Val Met Glu Glu
        420                 425                 430
Val Val Arg Arg Asp Lys Asn His Pro Ala Val Val Met Trp Ser Val
    435                 440                 445
Ala Asn Glu Pro Ala Ser His Leu Glu Ser Ala Gly Tyr Tyr Leu Lys
        450                 455                 460
Met Val Ile Ala His Thr Lys Ser Leu Asp Pro Ser Arg Pro Val Thr
465                 470                 475                 480
Phe Val Ser Asn Ser Asn Tyr Ala Ala Asp Lys Gly Ala Pro Tyr Val
            485                 490                 495
Asp Val Ile Cys Leu Asn Ser Tyr Tyr Ser Trp Tyr His Asp Tyr Gly
            500                 505                 510
His Leu Glu Leu Ile Gln Leu Gln Leu Ala Thr Gln Phe Glu Asn Trp
        515                 520                 525
Tyr Lys Lys Tyr Gln Lys Pro Ile Ile Gln Ser Glu Tyr Gly Ala Glu
        530                 535                 540
Thr Ile Ala Gly Phe His Gln Asp Pro Pro Leu Met Phe Thr Glu Glu
545                 550                 555                 560
Tyr Gln Lys Ser Leu Leu Glu Gln Tyr His Leu Gly Leu Asp Gln Lys
            565                 570                 575
Arg Arg Lys Tyr Val Val Gly Glu Leu Ile Trp Asn Phe Ala Asp Phe
            580                 585                 590
Met Thr Glu Gln Ser Pro Thr Arg Val Leu Gly Asn Lys Lys Gly Ile
        595                 600                 605
Phe Thr Arg Gln Arg Gln Pro Lys Ser Ala Ala Phe Leu Leu Arg Glu
    610                 615                 620
Arg Tyr Trp Lys Ile Ala Asn Glu Thr Arg Tyr Pro His Ser Val Ala
625                 630                 635                 640
Lys Ser Gln Cys Leu Glu Asn Ser Pro Phe Thr
            645                 650

<210> SEQ ID NO 12
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 12

Cys Ser Asn Arg Asp Ala Arg Arg Cys
1               5

<210> SEQ ID NO 13
<211> LENGTH: 13
<212> TYPE: PRT
<213> ORGANISM: Artificial sequence
<220> FEATURE:
<223> OTHER INFORMATION: Synthetic polypeptide
```

```
<400> SEQUENCE: 13

Cys Asn Gly Arg Cys Val Ser Gly Cys Ala Gly Arg Cys
1               5                   10

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 14
tatgctgggg cccagccggc c                                        21

<210> SEQ ID NO 15
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 15
ctgagatgag tttttgttcg tcgac                                    25

<210> SEQ ID NO 16
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (19)..(19)
<223> OTHER INFORMATION: s is g or c

<400> SEQUENCE: 16
cgagtatgga gcagaannsa ttgcagggtt tcaccaggat cc                 42

<210> SEQ ID NO 17
<211> LENGTH: 42
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(24)
<223> OTHER INFORMATION: s is g or c
<220> FEATURE:
<221> NAME/KEY: misc_feature
<222> LOCATION: (25)..(26)
<223> OTHER INFORMATION: n is a, c, g, or t

<400> SEQUENCE: 17
ggatcctggt gaaaccctgc aatsnnttct gctccatact cg                 42

<210> SEQ ID NO 18
<211> LENGTH: 62
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(25)
<223> OTHER INFORMATION: n is a, c, g, or t
```

```
<220> FEATURE:
<221> NAME/KEY: misc_feature
<222> LOCATION: (26)..(26)
<223> OTHER INFORMATION: s is g or c
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (38)..(38)
<223> OTHER INFORMATION: s is g or c

<400> SEQUENCE: 18
ggaattttgc cgatttcatg actnnscagt caccgnnsag agtgctgggg aataaaaagg      60
gg                                                                    62

<210> SEQ ID NO 19
<211> LENGTH: 61
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (24)..(24)
<223> OTHER INFORMATION: s is g or c
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (36)..(36)
<223> OTHER INFORMATION: s is g or c
<220> FEATURE:
<221> NAME/KEY: misc_feature
<222> LOCATION: (37)..(38)
<223> OTHER INFORMATION: n is a, c, g, or t

<400> SEQUENCE: 19 cccctttta ttcccagcac tctsnncggt gactgsnnag tcatgaaatc ggcaaaattc       60
c                                                                     61

<210> SEQ ID NO 20
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 20
ctggggccca gccggccagt gaagtg                                          26

<210> SEQ ID NO 21
<211> LENGTH: 54
<212> TYPE: DNA
<213> ORGANISM: Artificial sequence
<220> FEATURE:
<223> OTHER INFORMATION: synthetic oligonucleotide

<400> SEQUENCE: 21
atatctagat ccgccgccac ccgacccacc acctcctgaa ccgcctccac gttt           54
```